US009012872B1

(12) United States Patent
Fang et al.

(10) Patent No.: US 9,012,872 B1
(45) Date of Patent: Apr. 21, 2015

(54) AUTO-CALIBRATED SCANNING-ANGLE PRISM-TYPE TOTAL INTERNAL REFLECTION MICROSCOPY FOR NANOMETER-PRECISION AXIAL POSITION DETERMINATION AND OPTIONAL VARIABLE-ILLUMINATION-DEPTH PSEUDO TOTAL INTERNAL REFLECTION MICROSCOPY

(75) Inventors: Ning Fang, Ames, IA (US); Wei Sun, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 345 days.

(21) Appl. No.: 13/006,739

(22) Filed: Jan. 14, 2011

Related U.S. Application Data

(60) Provisional application No. 61/295,568, filed on Jan. 15, 2010, provisional application No. 61/384,095, filed on Sep. 17, 2010.

(51) Int. Cl.
*G01N 21/64* (2006.01)
(52) U.S. Cl.
CPC ........ *G01N 21/6428* (2013.01); *G01N 21/6458* (2013.01)
(58) Field of Classification Search
USPC ............................................ 250/461.2, 461.1
See application file for complete search history.

(56) References Cited

U.S. PATENT DOCUMENTS

| | | | |
|---|---|---|---|
| 4,621,911 A | | 11/1986 | Lanni et al. |
| 4,899,283 A | * | 2/1990 | Annis ................................ 378/7 |
| 6,055,097 A | | 4/2000 | Lanni et al. |
| 6,255,642 B1 | * | 7/2001 | Cragg et al. .................. 250/216 |
| RE38,307 E | | 11/2003 | Gustafsson et al. |
| 6,751,018 B2 | | 6/2004 | Kawano et al. |
| 7,154,598 B2 | * | 12/2006 | Montagu et al. .............. 356/244 |
| 7,297,961 B2 | | 11/2007 | Kang et al. |
| 7,369,308 B2 | | 5/2008 | Tsuruta et al. |
| 2004/0196457 A1 | | 10/2004 | Aono et al. |
| 2005/0057798 A1 | | 3/2005 | Osborne et al. |
| 2005/0062974 A1 | * | 3/2005 | Ivarsson ....................... 356/445 |
| 2006/0280404 A1 | | 12/2006 | Kennedy et al. |
| 2007/0052958 A1 | | 3/2007 | Ulrich et al. |
| 2008/0231834 A1 | * | 9/2008 | Gryczynski et al. ............ 356/36 |
| 2009/0237501 A1 | | 9/2009 | Lemmer et al. |

OTHER PUBLICATIONS

Sun, Wei, et al., "Autocalibrated Scanning-Angle Prism-Type Total Internal Reflection Fluorescence Microscopy for Nanometer-Precision Axial Position Determination", Analytical Chemistry, vol. 82, No. 6, Mar. 15, 2010, pp. 2441-2447.

* cited by examiner

*Primary Examiner* — David Porta
*Assistant Examiner* — Edwin Gunberg
(74) *Attorney, Agent, or Firm* — McKee, Voorhees & Sease, P.L.C.

(57) ABSTRACT

A method, apparatus, and system for improved VA-TIRFM microscopy. The method comprises automatically controlled calibration of one or more laser sources by precise control of presentation of each laser relative a sample for small incremental changes of incident angle over a range of critical TIR angles. The calibration then allows precise scanning of the sample for any of those calibrated angles for higher and more accurate resolution, and better reconstruction of the scans for super resolution reconstruction of the sample. Optionally the system can be controlled for incident angles of the excitation laser at sub-critical angles for pseudo TIRFM. Optionally both above-critical angle and sub critical angle measurements can be accomplished with the same system.

50 Claims, 17 Drawing Sheets

AUTO-CALIBRATED SCANNING-ANGLE PRISM-TYPE TOTAL INTERNAL REFLECTION MICROSCOPY FOR NANOMETER-PRECISION AXIAL POSITION DETERMINATION AND OPTIONAL VARIABLE-ILLUMINATION-DEPTH PSEUDO TOTAL INTERNAL REFLECTION MICROSCOPY

CROSS-REFERENCE TO RELATED APPLICATIONS

This application claims priority under 35 U.S.C. §119 to provisional application Ser. No. 61/295,568 filed Jan. 15, 2010 and Ser. No. 61/384,095 filed Sep. 17, 2010, herein incorporated by reference in their entireties.

GRANT REFERENCE

This invention was made with government support under Contract No. DE-AC02-07CH11358 awarded by U.S. Department of Energy. The government has certain rights in the invention.

I. BACKGROUND OF THE INVENTION

A. Field of the Invention

The present invention relates to microscopy and, in particular, to total internal reflection microscopy (TIRM) and to prism-type variable-angle TIRM (sometimes referred to as VA-TIRM). The invention can include a pseudo total internal reflection microscopy mode. One type of TIRM 15 TIRFM (Total Internal Reflection Fluorescence Microscopy (conventional or pseudo)), which creates an evanescent field (EF) and gathers fluorescence generated by the EF. Another type of TIRM gathers Raman scattering. Another type gathers scattered light from plasmonic materials including nano-particles. Another investigates plasmon surface resonance.

The invention relates to use of scanning single-prism-type TIR microscopy for collection of any of a variety of scattered radiation or another signal, including but not limited to study of fluorescence, surface plasmon scattering spectra, Raman spectra, plasmonic materials or particles, or analogous effects or phenomena.

B. Related Art

TIRFM is a well-known type of TIR microscopy. TIRFM takes advantage of an optical effect that can be adapted to observe fluorescent events occurring at the interface between two optical media of different refractive indices. Excitation light incident upon such a boundary, travelling at an angle greater than the critical angle, undergoes total internal reflection. The electromagnetic field of the total internal reflected light extends into the sample beyond the interface. Extending only several tens of nanometers into the second medium of lower refractive index, typically along the optical axis of the microscope in essentially the z direction, this evanescent field decreases exponentially in intensity along the z-axis of penetration. Only the section of the specimen located within the evanescent field undergoes fluorescence excitation. Although TIRFM is limited to the area within several hundreds of nanometers of the substrate/sample interface where total internal reflection is occurring, it is an increasingly popular technique for visualizing, with high signal-to-noise ratio, nano-scale structures. One particularly important application is visualizing and imaging processes that occur in and around the membrane of living cells (partially due to availability of novel membrane-specific fluorophores). TIRFM is also a common technique for imaging single molecules dynamics.

Two typical TIRFM techniques are known as objective-type and prism-type. The objective-type approach requires that the laser be introduced through the microscope objective, and the angle over which TIR can be practically achieved requires use of an oil-immersion objective (with big numerical aperture or N.A.). Also, the objective configuration can result in limitations of available angle range for incident illumination light. General principles of TIRFM in the context of objective-type TIRFM can be found at U.S. RE38,307, incorporated by reference herein. The present invention relates to prism-type TIRFM.

Prism-type TIRFM illuminates a sample on a prism with an evanescent field layer at the prism/sample interface. Typically a laser light is directed through a prism to the sample, wherein the angle of incidence of the laser results in total internal reflection at that prism/sample interface. An evanescent field layer is generated from the prism/sample interface. (Sometimes, the sample can be put on a glass slide which is put on the top of prism. Then the evanescent field will happen at the slide/sample interface.) The thickness of the field is dependent on the angle of incidence and the frequency of laser light. Adjusting those parameters, structures of a much smaller scale in the sample, within the depth of the evanescent field, can be resolved than with regular light microscopes. The evanescent field technique suppresses background to get better contrast and thus better resolution of smaller features. The higher resolution is substantial compared to other normal light microscopes, e.g., epi-fluorescence, or bright field microscope. General principles regarding prism-type TIRFM can be found at U.S. published patent application US2005/0057798 and U.S. Pat. No. 6,255,642, each incorporated by reference herein.

Electron microscopes are an alternative for resolution of submicron or nanoscale features. However, the systems are quite expensive. Additionally, they require drying and exposure of the sample to vacuum. This prevents such things as observing live cells. Therefore, electron microscopes are not indicated for the study of live cells, which is in increasingly greater demand. Observation of live cells may lead to a better understanding of cells and their functions, and thus lead to substantial advancements, including but not limited to, biology, medicine, and other sciences.

There is a need for better resolution than existing microscopy techniques with respect to many applications which can be flexible, adaptable, effective, and more economical than, for example, electron microscopes. There have been attempts to obtain sub-diffraction-limited spatial information with a different approach than the present invention. See, for example, U.S. published application 2009/0237501, incorporated by reference herein. It describes some of the hurdles as well as some of the benefits and applications of the ability to do so.

The principles of TIRFM are well-known. A variety of manufacturers (e.g. Nikon, Zeiss, Olympus) provide commercially-available objective-type TIRFM systems. Such systems can include not only a light microscope, but also a programmable controller and/or computer that can communicate with such things as electronically-controller mirror turrets, stages, illumination sources, displays, and cameras.

In TIRFM, a sample (e.g. live cells) suspended in a liquid or semi-liquid phase substance) is placed on a glass microscope slide. A source of coherent light is directed at an angle of incidence such that it has total internal reflection (TIR) (the light does not refract and pass through the slide). A standing wave at the slide/sample interface creates a very thin evanescent layer above the interface. By varying angle of incidence (variable angle or VA) of the illuminating light, the thickness of the layer is changed. One can see or resolve through the microscope things at varying vertical (axial to the microscope objective) distances from the interface. Thus, one can not only resolve very small individual particles or features within that layer not possible with a normal light microscope, but can vary the thickness of the layers so features can be resolved at different vertical (axial) distances from the interface surface. Thus, varying angle of incidence of the illuminating light can essentially section the sample on the slide by changing that angle of incidence systematically.

But there are issues with present VA-TIRFM technology. For example, performance of present systems largely depends on the accuracy, precision, and reproducibility of tedious, time-consuming re-calibration procedures before each sample is imaged. This limits the through-put and efficiency of such systems. It also exposes such systems to unintentional human error. The theoretical spatial resolution of evanescent field (EF) excitation has not been harvested because it is difficult or impossible to manually calibrate the system at all relevant incident angles within small margins of error. Also, use of such TIRFM systems for 3D image reconstruction has been hampered by difficulties performing full Laplace transforms or fitting with nonlinear least squares methods. Many TIRFM systems do not have any systematic way to step the excitation plane through the sample. Another issue that arises with TIRFM are limitations regarding illumination depth.

One or more similar issues to those discussed above exist regarding TIR microscopy relevant to Raman scattering, plasmonic scattering, surface plasmon resonance, and analogous effects or phenomena.

Therefore, there is room for valuable improvement in these technical areas.

II. SUMMARY OF THE INVENTION

It is therefore a principle object, feature, aspect, or advantage of the present invention to provide improvements or advances over the state of the art.

Other objects, features, aspects, or advantages of the present invention include a VA-TIRM system, methodology, or apparatus which provides one or more of:
  a. quick and automatic creation of an evanescent field or other effect for any incident angles in the full range of relevant angles;
  b. fast re-calibration for each sample;
  c. fast scan through a relevant set of angles;
  d. optionally plural-color auto-calibration and scanning (e.g. at least dual-color) with multiple light sources with one microscope;
  e. fine adjustment of optical trapping forces created by the evanescent field.
  f. high axial resolution;
  g. flexibility and adaptability to a wide variety of applications;
  h. economy and efficiency; and
  i. improved ability to study cellular organization and dynamic processes, single-molecule dynamics, or other applications because of improved axial resolution.

These and other objects, features, aspects, or advantages of the present invention will become more apparent with reference to the accompanying specification and claims.

One aspect of the present invention comprises a method of VA-TIRM which uses an automatic calibration algorithm to improve set-up and accuracy.

Another aspect of the present invention comprises a method of VA-TIRM which uses automatic scanning of one or more light sources through any set of relevant incident angles to improve system operation and results.

Another aspect of the present invention comprises a VA-TIRM system which comprises components for one or more color VA-TIRM and one or both of automatic calibration and scanning.

Another aspect of the present invention comprises a VA-TIM system which comprises a software program and controller to facilitate automatic calibration and/or scanning.

Another aspect of the invention provides for variable illumination depth pseudo total internal reflection fluorescence microscopy. In one example, the automatic calibration and angle-scanning prism-type total internal reflection fluorescence microscope (TIRFM) described above according to other aspects of the invention can be modified to function both as TIRFM and pseudo TIRFM. When the incident angle of the excitation laser beam is controlled to be larger than the critical angle, the instrument can function in variable-angle pseudo TIRFM mode. When incident angle is reduced to be in sub critical range, the instrument can operate in pseudo TIRFM mode. The illumination depth in pseudo TIRFM can be controlled through changing the incident angle or the horizontal position of the laser spot. Substantial scanning ranges are possible. An example of benefits include the ability to provide improved illumination depth for and scanning of such things as whole cells.

Another aspect of the invention provides for TIRM relative to Raman scattering, plasmonic scattering, surface plasmon resonance, and analogous phenomena.

III. BRIEF DESCRIPTION OF THE DRAWINGS

FIG. 1C is a graphic user interface (GUI) of software according to an exemplary embodiment of the present invention, illustrating features such as automatic calibration and scanning.

FIG. 7 is another example of the GUI of FIG. 1C.

IV. DETAILED DESCRIPTION OF EXEMPLARY EMBODIMENTS

A. Overview

For a better understanding of aspects of the present invention, examples of forms the invention can take will now be described in detail. The context of the examples will be explained relative to each example. The various examples of the invention use similar general methodology and apparatus for improved VA-TIRFM. It is to be understood, however, that the invention is not limited to these specific illustrative examples. The invention can be applied to other samples and/or applications in analogous ways.

A pseudo TIRFM mode example is also disclosed.

B. Exemplary Embodiment One

1. Overview of Exemplary System 10

Figure 1A:
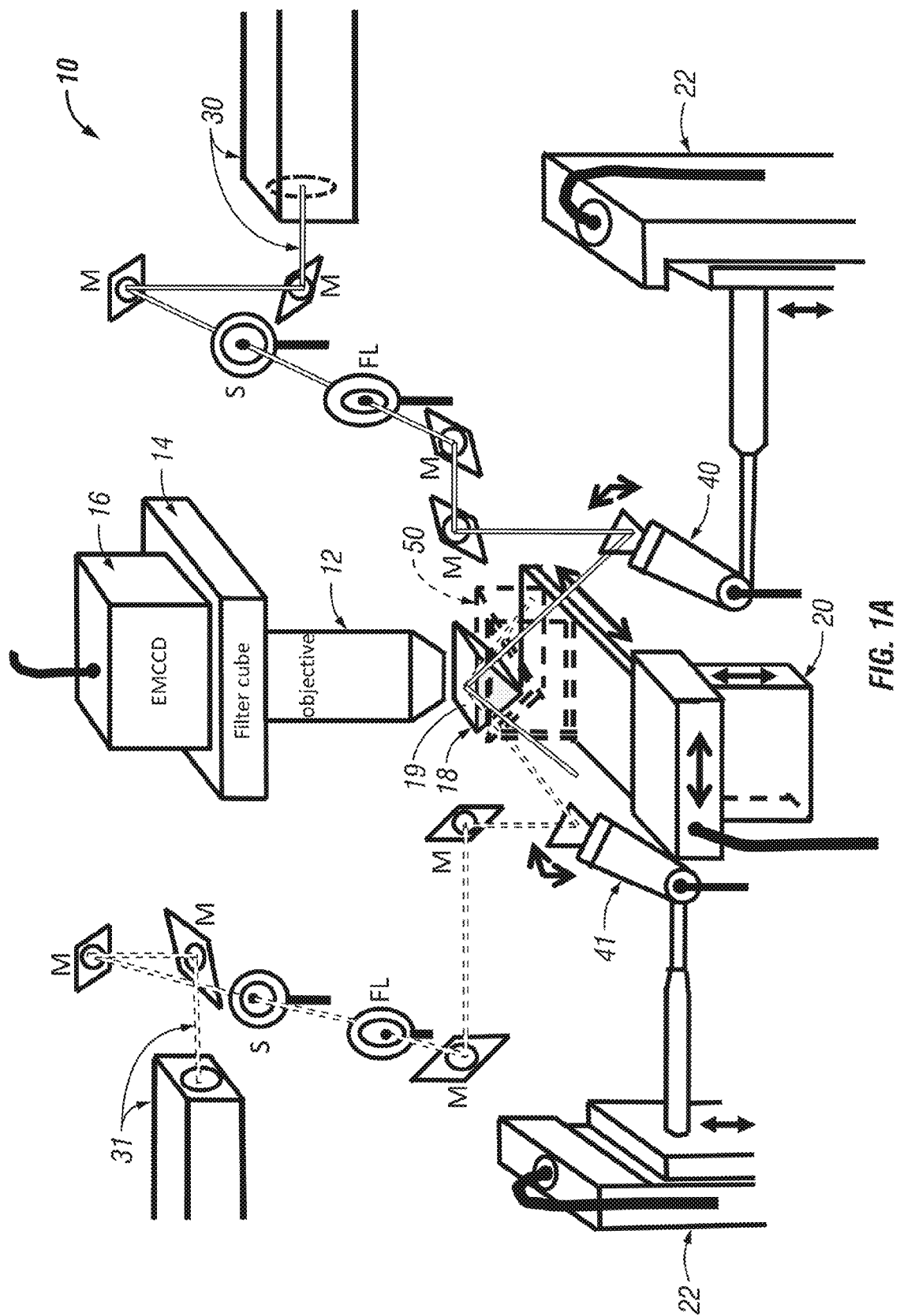
FIG. 1A is a schematic view of certain components of a VA-TIRFM dual-color imaging microscope according to one exemplary embodiment of the present invention.

In this example, the system (referred to generally as system 10) utilizes the components diagrammatically indicated at FIGS. 1A-D. A novel VA-TIRFM type microscope set-up is as illustrated in FIG. 1A. A conventional objective lens 12, filter 14, and cm camera 16 are optically aligned along the axis of objective 12 (e.g. Nikon optiphot-2 microscope with Plan Fluor 100×/NA 1.3 objective; Andor iXon$^{EM}$+897 EMCCD with 512×512 imaging array, 16 μm pixel size). A prism 18 (e.g. Melles Griot EDP-25.0-UV equilateral-type, 25 mm, fused silica prism) is appropriately positioned base up along the objective's axis on a prism/sample holder 50 (see FIGS. 1F-H). A microscope slide or cover slip with a sample to be observed/imaged (not shown) would be placed on the slide/cover slip holder portion 54 of prism/sample holder 50 at the exterior surface of the prism base 19. The holder 50 has a base 52 which can be mounted on translational stage 20 (e.g. and held in position by alignment means such as slots 56 or other fastening or positioning structure). Prism holder slots 56 in generally parallel arms extending from base 52 are configured to receive and hold prism 18 in a "base up" position. The base 19 of prism 18 would be automatically positioned at or just below the plane of a slide or cover slip placed in slide/cover slip holder 54. This prism/sample holder thus can be a multi-function, pre-manufactured device that facilitates the TA-TIRFM microscopy of system 10. Also, in this example, conventional microscope stage is replaced with more precise translational stage 20 (Sutter MP-285 31) translational stage) to move the prism and slide relative to the objective's axis.

In this example, a coherent light source, laser 30 of a first frequency or color (e.g. Coherent 40-mW 640-nm solid-state continuous wave), can have its angle of incidence to a slide on stage 20 adjusted by controlling the position of a mirror galvanometer 40 (e.g. Cambridge Technology 6220 and 6220H). The beam from laser 30 is first directed through a set of optics (comprised of mirrors M, a shutter S (e.g. Uniblitz LS2Z2), and focusing lens FL of FIG. 1A). Mirror galvanometer 40 then directs the beam into a side face of prism 20. Motorized linear stage 22 (Newport MAA-PP motorized linear stage) and mirror galvanometer 40 can be controlled to change position of the mirrors of mirror galvanometer 40 to change each beam's direction relative to prism 18, which changes its angle of incidence with the internal side of base surface 19 of prism 18. This changes the angle of incident of TIR in prism 18, and thus changes the depth of the evanescent field caused by the TIR at the slide/sample interface.

In this example, a second laser 31 (e.g. Uniphase 45-mW 532-nm solid-state continuous wave), with the same set of optics M, S, and FL, a controllable mirror galvanometer 41, and a motorized linear stage 22 directs the second laser beam (a different frequency/color) into another side face of prism 18 so that there is TIR at the same point of the slide/sample interface as laser 30. Thus, system 10 provides the ability, if both lasers 30 and 31 are operated, for two color VA-TIRFM with the same microscope.

As can be appreciated, set up of system 10 would include selection of location of lasers 30 and 31 relative to the microscope, correct positioning of prism/sample holder 50 on stage 20, and positioning of a slide or cover slip on holder 50 and adjustment of stage 20 and objection lens 12 appropriately. Mirror galvanometers are also positioned to allow control of lasers 30 and 31 relative to prism 18 to allow a desired range of TIR angles for each laser 30 and 31 relative to the sample/slide interface (the slide or cover slip holding the sample being positioned at the plane of base 19 of prism 18).

Importantly, as indicated at FIG. 1A, this provides a prism-based TIRFM system which enables very precise control of angle of incidence of either laser beam 30 or 31 relative to the slide/sample interface. Motorized linear stage and mirror galvanometers are capable of very precise (nanometer scale) movement or adjustment, which can in turn allow very small incremental scanning of angle of incidence of either or both beams relative to the slide/sample interface.

Figure 1B:
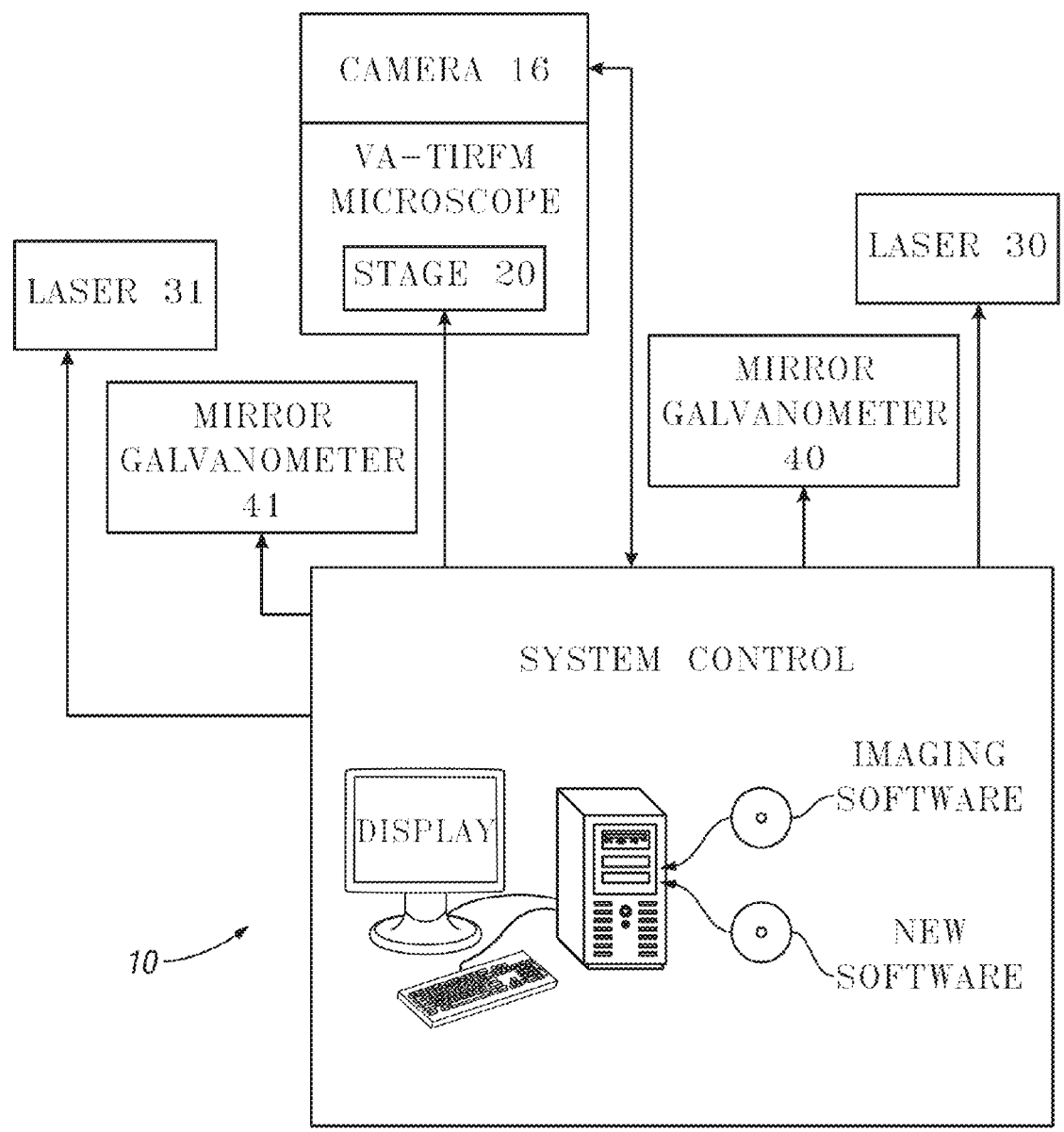
FIG. 1B is a block diagram of a complete VA-TIRFM system including the microscope of FIG. 1A and associated VA-TIRFM components such as a computer and display, imaging software, etc.

As indicated at FIG. 1B, the complete system 10 includes components that allow programmable control of at least the relative position of stage 22, and orientation of mirror galvanometers 40 and 41 to the position of the sample on a slide. Conventional imaging software operable with camera 16 operates with a novel program to allow features such as automatic calibration and automatic scanning, as while be further described below.

More specifically, as indicated at FIG. 1B, system control can include the new software which can control small, precise incremental adjustment of mirror galvanometers 40 and 41. This allows small, precise, repeatable scanning of lasers 30 and 40 through plural angles of incidence. The program is configured to provide automatic calibration and automatic scanning functions, as will be described in detail later herein.

2. Features of System 10

Following is a detailed description of aspects of the invention and how to make and use exemplary embodiments of the invention. Much of this information can be also found in Sun, W., Marchuk, Wang, G., and Fang, N., "Auto-calibrated Scanning-Angle Prism-Type Total Internal Reflection Florescence Microscopy for Nanometer-Precision Axial Position Determination", Anal. Chem., Vol. 82, No. 6, Mar. 15, 2010, which is incorporated by reference herein.

An automatic calibration and scanning-angle prism-type total internal reflection fluorescence microscope (TIRFM) was constructed and tested for the highest vertical resolution. The angle of the incident laser beam can be changed automatically and reliably from subcritical angles to nearly 90° with intervals smaller than 0.2°, and the laser illumination spot in the sample can be calibrated to automatically overlap with the center of the microscope's field of view. By scanning through a wide range of incident angles with different evanescent-field layer thicknesses, the fluorescence intensity decay curves of randomly distributed fluorescent nanospheres in agarose gel were obtained and fitted with the theoretical decay functions to determine their vertical positions. The best axial resolution was demonstrated to be better than 10 nm under the rigorous statistical analysis of confidence levels and by the Monte Carlo simulation. The new setup was further utilized to determine the tilting angle of the microtubules buried in agarose gel and to find the precise surface plasmon resonance (SPR) angle for gold film enhanced TIRFM. We demonstrate the new microscope's unique capability to find the best illumination configuration for complex systems automatically and reproducibly.

Figure 1C:
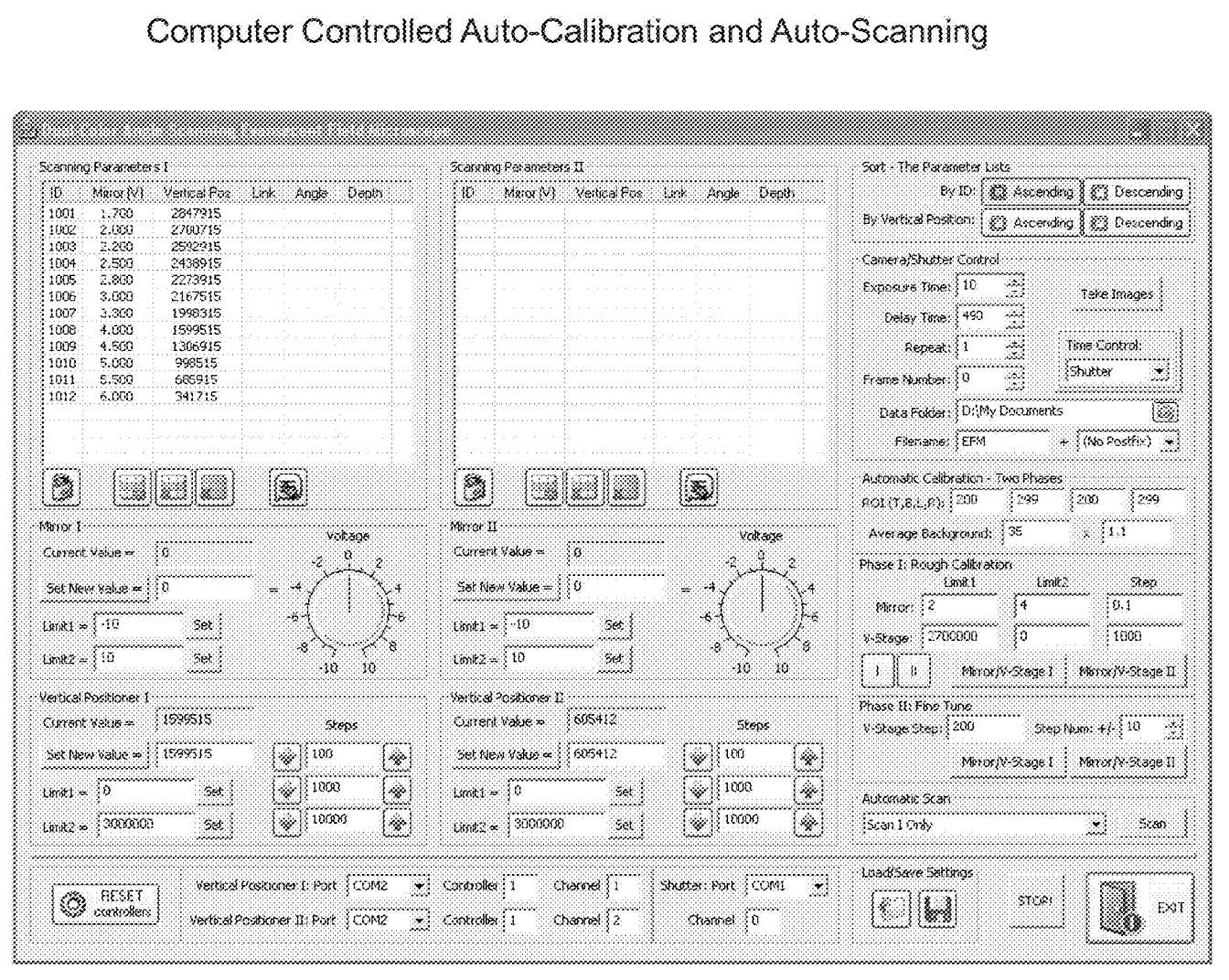
Figure 1D:
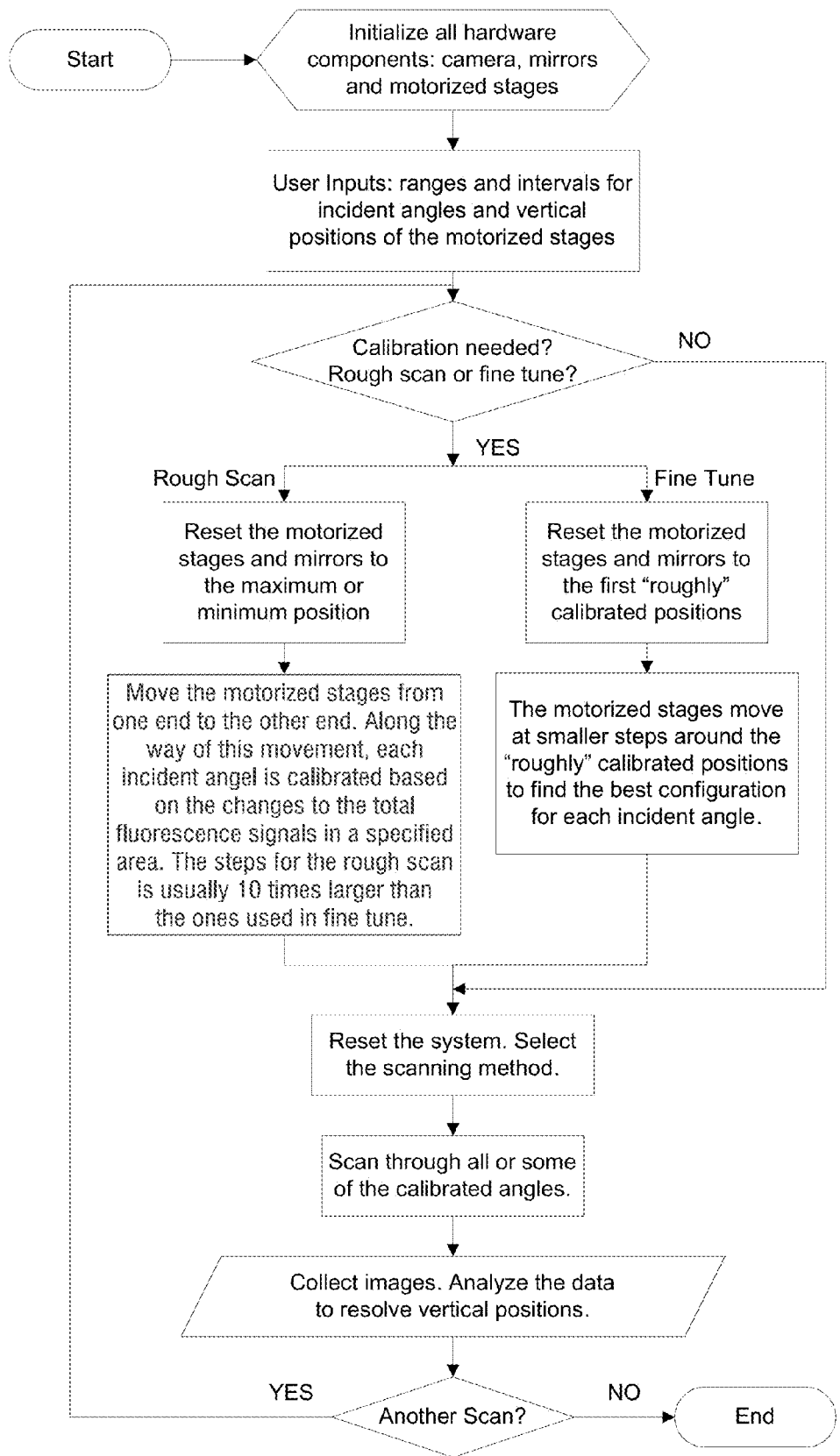
FIG. 1D is a flow chart of operation of the exemplary software.

The flow of the new program is illustrated at FIG. 1D. A graphic user interface (GUI) used with the program is shown at FIG. 1C. As will be described in more detail later, the program has the following main steps:

Hardware components are first initialized.

The user is allowed ranges and intervals for incident angles and vertical positions.

The user selects if calibration (or re-calibration) is needed (e.g. for each new sample); and then, importantly, whether or not coarser or finer calibration is preferred.

The selected coarse (or "rough") or fine scan is automatically instigated where the system control steps the lasers, via control of the mirror galvanometers (or other precisely controllable actuators), through incremental angles of incidence over a range while monitoring total fluorescence signals in a specified area. This combination allows quick, automatic calibration across a range of critical angles of incidence of interest. Rough or fine scale calibration, or both, can be selected by the user, or can be automatically performed. Upon calibration, the user or the system control selects a scanning procedure (again controlling the calibrated angles over a pre-determined range), operates the camera to collect images for each scan, and facilitates analysis of data in the acquired images to resolve vertical or axially positions.

The GUI of FIG. 1C gives one example of user control and monitoring. Note how the user can select automatic calibration parameters for both rough and fine procedures, as well as select an automatic scanning procedure. Other selections are self-evident. The scanning parameters are displayed to the user. Camera/shutter controls, as well as vertical positioner controls, are presented also.

3. Introduction to Exemplary Embodiment One

Total internal reflection fluorescence microscopy (TIRFM) has become an indispensable tool to study cellular organization and dynamic processes that occur near the cell culture and glass substrate interface.[1] It has also been used extensively to study molecular dynamics, including diffusion[2-4] and absorption[5-6], at liquid/solid interfaces. All of these applications rely on TIRFM's ability to selectively excite fluorophores very close to the interface while minimizing background fluorescence from out-of-focus planes. An evanescent field (EF) is produced when an incident light beam travelling from a medium of high refractive index ($n_1$) into a medium of low refractive index ($n_2$) at an incident angle ($\theta$) greater than the critical angle ($\theta_c$), which is defined as $\theta=\sin^{-1}(n/n)$. The EF intensity (I) exponentially decays with the vertical distance (z) from the interface, and drops to 1/e of the value at the interface over the penetration depth (d): $I(z)=I(0)e^{-z/d\theta}$. The d value is well defined by Equation 1 for a given interface as it depends theoretically only on $\theta$ and the wavelength ($\lambda$) of the incident light.

$$d(\theta) = \frac{\lambda}{4\pi\sqrt{(n_1\sin\theta)^2 - n_2^2}}, \quad (1)$$

However, the characteristic EF depth in an actual sample may deviate from theoretical values for several reasons, including the polarization of the excitation light, the orientation of the dipoles, the unevenness of light illumination, refractive index mismatch, non-uniform fluorescence emission near a dielectric surface, optical interference between the direct and reflected emission beams, imperfect collimation of the laser beam, and imperfect alignment of the optical components. Therefore, experimental calibration is necessary for quantitative analysis of fluorescence signals.

The calibration of the evanescent field in a homogeneous sample can be carried out with quantum dots or fluorescent beads on the tip of an AFM arm[7] or a graphite pencil[8] or a patch pipette[9], fluorescent beads attached onto a convex lens or settled on a cell surface[10], large spherical beads (8.85 μm diameter) on a flat glass slide[11], a known fluorophore distribution between a convex lens and a flat prism surface[12], or tilted microtubules in gel[13]. With the calibration data, axial distances can then be estimated with much improved accuracy in a number of different means. The ratio of fluorescence intensities from sequential acquisitions with fixed angle TIRFM and wide-field (WF) microscopy[14-15] or from two-angle TIRFM[16] can give good estimates of axial distances, while more depth-resolved information is obtainable with prism or objective-based variable-angle (VA) TIRFM[4, 12-13, 17-18] in which a stack of multi-angle images contains the integrated fluorescence intensity over various thicknesses of the sample.

The prism-type VA-TIRFM generally provides several benefits over its objective-based counterpart, such as a wider range of incident angles, higher accuracy in incident angle determination, less excitation light scattering, and lower cost. In a typical prism-based VA-TIRFM system, a set of rotatable mirrors and micro-stepper motors are used to direct the center of the laser beam onto a specified spot on a sample at a wide range of incident angles. The parameters are recorded and later used to capture images at these calibrated incident angles. Recalibration is often necessary before a new sample is imaged. The performance of the system largely depends on the accuracy, precision, and reproducibility of the tedious, time-consuming calibration procedure.

In the present work, we introduce a new auto-calibration scanning-angle TIRFM setup. An optimized system layout and an automatic high-precision calibration procedure are implemented to find the incident angles in the full range (from subcritical angles to nearly 90°) with intervals smaller than 0.2°. The entire auto-calibration procedure can be finished within minutes. At each incident angle, the automatic calibration (or re-calibration) was designed to overlap the center of laser illumination spot with the center of the microscope field of view. Once calibrated, the system scans through the whole range of incident angles reliably and reproducibly, and the measured fluorescence intensities follow the decay functions more closely with smaller relative errors than any other existing VA-TIRFM system, resulting in better practical resolution in the axial direction.

To demonstrate the precision of the system, we used the new microscope to find the exact incident angle that produced the most intense evanescent field for a given interface between a gold-film-coated coverslip and aqueous solution while a p-polarized (in the plane of incidence formed by the incident and reflected beams) incident laser beam was used. To demonstrate the high axial resolution in practice, we resolved fluorescent nanospheres buried in agarose gel at different vertical positions. The new microscope was further applied to image tilted fluorescent microtubules in agarose gel.

4. Experimental Section

Imaging System.

FIG. 1A shows the schematic representation of the apparatus 10 that was designed and built. A Nikon Optiphot-2 microscope equipped with a Plan Fluor 100×/NA 1.3 objective 12 and an Andor iXon$^{EM}$+897 camera 16 (Belfast, Northern Ireland; 512×512 imaging array, 16 μm×16 μm pixel size) were used as the centerpiece. In order to reduce the sample drifting, the original microscope stage 20 was replaced by a Sutter MP-285 motorized high precision three-dimensional translational stage (Novato, Calif.). An equilateral fused silica prism 18 (Melles Griot, Albuquerque, N. Mex.) was housed in a prism holder 50 (see FIGS. 1F-H) that was fixed on the Sutter stage 20. A 40-mW 640-nm solid-state continuous wave (CW) laser 30 or 31 (Coherent, Santa Clara, Calif.) and a 45-mW 532-nm solid-state CW laser (Uniphase, San Jose, Calif.) were employed for excitation. Nearly identical arrangements of the optics and motorized stages were set up on both sides of the prism 18 to direct laser beams 30, 31 towards the imaging area. On either side, the laser beam was first pointed to a periscope, passed through a Uniblitz mechanical shutter (model LS2Z2, Vincent Associates, Rochester, N.Y.) and a focusing lens (15-cm focal length), and then was directed towards the mirror of a galvanometer optical scanner 40 or 41 (model 6220, Cambridge Technology, Cambridge, Mass.). The focusing lens was used to control the laser spot size in the imaging area. The mirror galvanometer 40 or 41 was coupled to a high precision motorized linear stage (model MAA-PP, Newport, Irvine, Calif.), and directed the focused laser beam through the equilateral prism to the liquid-solid interface at different incident angles.

FIG. 1B provides a schematic block diagram of the whole system 10, including a conventional computer with commercially-available imaging software, and input/output (I/O) interface to communicate with other system components (e.g. controllers for adjustable mirrors 40 and 41, stage 20, shutters S, lasers 30 and 31, etc.). Operative connection of these components is within the skill of those skilled in this technical art. The main computer also includes the novel software program for automatic calibration and scanning with system 10, as will now be described in detail.

FIG. 1C illustrate a GUI for the new software. As can be appreciated by those skilled in the art, this GUI provides the operator with visual summary of the operational parameters of the new software as well as prompts for providing the software values for those operational parameters. As will be discussed below, the new software enables many benefits for VA-TIRFM.

FIG. 1D is a flow diagram of the new software.

Below are descriptions of specific uses and applications of system 10 and its new software.

Automatic Angle Scanning and Vertical Position Calibration. Negatively charged 28 nm diameter fluorescent nanospheres (Duke Scientific, Palo Alto, Calif.) were used to calibrate the incident angles. These nanospheres were immobilized on the positively charged prism surface modified with poly-L-lysine (PLL). The collected fluorescence intensity at a given incident angle depends on the horizontal position of the laser spot on the prism surface. Only when the center of the laser spot overlaps perfectly with the center of the objective lens, the fluorescence intensity is at the highest level. Furthermore, only if the overlapping of two centers is consistently achieved at all incident angles, the angle scanning process can generate highly reproducible depth information of objects located in the EF. The new computer program was developed to automatically optimize the horizontal position of the laser spot at each incident angle.

The new computer program carries out the calibration in two rounds: rough scan and fine tune. To maintain high precision, the motorized linear stage 20 travels step by step in only one direction. The fluorescence images are recorded by the EMCCD camera 16 at each step. This is consistent during both rounds of calibration. During the rough scan, the vertical step size is set to be relatively large to reduce the time required for a full scan, and the vertical positions of the mirror galvanometer 40 and/or 41 at all incident angles are obtained from each local maximum of the integrated fluorescence intensities in a chosen area. During the round of fine tune, the mirror galvanometer 40 and/or 41 is controlled to move around the "roughly-calibrated" positions again but with a smaller step size to obtain more precise vertical positions. Multiple rounds of fine tune can be carried out if desired. All these angles and vertical positions are recorded and can be reloaded when starting new experiments.

Coverslips Coated with Metal Films.

Coverslips (22 mm×22 mm, Zinc Titania glass, refractive index 1.523 at sodium D line, Corning, N.Y.) were thoroughly cleaned in an ultrasonic bath twice in Contrad 70 detergent solution (Decon Labs, King of Prussia, Pa.), 4 times in 18.2 MΩ pure water and twice in pure ethanol. Each cleaning step lasted 30 mins. After blown dry with pure nitrogen gas, the coverslips were deposited with 5 nm of chromium followed by 30 nm of gold in an Airco Temscal BJD 1800 E-beam evaporator (Berkeley, Calif.). The coverslips were immersed in 100 μg/ml poly-L-lysine (PLL) solution for 2 hours to generate positively charged surfaces. Negatively charged 28 nm diameter fluorescent nanospheres were diluted to proper concentration in 18.2 MΩ water containing an oxygen scavenging system, composed of 0.5 mg/ml glucose oxidase (Sigma), 40 μg/ml catalase (Sigma), 10% (w/v) glucose (Sigma) and 1% (v/v) β-mercaptoethanol (Fluka). The oxygen scavenging system was utilized to reduce photobleaching. The nanosphere solution was then loaded on a PLL-modified gold-coated coverslip and covered with a clean coverslip. The sample slide was placed on the prism surface.

Fluorescent Nanospheres Buried in Agarose Gel.

1.5% agarose gel was prepared by dissolving 1.5 mg agarose powder in 1 ml oxygen scavenging solution by heating in water bath. The gel solution was kept warm to avoid solidification. 28-nm fluorescent nanospheres were diluted to proper concentration in agarose gel solution. The gel solution was put on the surface of the TIRF prism and was quickly covered with a clean coverslip. The cooling gel solution trapped the nanospheres in random vertical positions as it solidified.

Tilted Fluorescent Microtubule in Agarose Gel.

Rhodamine labeled tubulin protein (Cytoskeleton, Denver, Colo.) was polymerized to form microtubules following the protocol provided by the manufacturer. The microtubules were diluted to a proper concentration in 1.5% agarose gel solution containing the oxygen scavenging system. The microtubule gel solution was then put on the surface of prism and quickly covered by a clean coverslip.

Results and Discussion

Determination of the z-position of a dye-doped nanosphere in angle-scanning TIRFM. For s-polarized incident light (the polarization direction perpendicular to the plane of incidence), the EF intensity at the interface (z=0) is:

$$I(0) = I_{in} \frac{4\cos^2\theta}{1 - n_2^2/n_1^2}, \quad (2)$$

where $I_{in}$ is the intensity of the incident light. When a dye-doped nanosphere is placed in the EF, the total emitted fluorescence is:

$$F(\theta) = k\varepsilon q \int_{z1}^{z2} w(z)I(0)e^{z/d(\theta)} dz = k\varepsilon I_{in} \frac{4\cos^2\theta}{1 - n_2^2/n_1^2} \int_{z1}^{z2} w(z)e^{z/d(\theta)} dz, \quad (3)$$

where k is a constant instrumentation factor; E is the molar extinction coefficient of the fluorophore; q is the quantum efficiency; w(z) is the number of the dye molecules in the layer at the vertical position z. When the size of the nanosphere is small enough compared to the penetration depth and the dye molecules are homogeneously doped, the geometrical center of the nanosphere nearly overlaps with the center of fluorescence.[8] The integral term in Equation 3 can be simplified to:

$$F(\theta) = k\varepsilon q I_{in} \frac{4\cos^2\theta}{1 - n_2^2/n_1^2} c(z) V e^{z/d(\theta)} = B\cos^2\theta e^{z/d(\theta)}, \quad (4)$$

where V is the volume of the nanosphere; c(z) is the concentration of the dye molecules in the sphere; B is a constant to account for all the variables that remain unchanged in Equation 4. Thus, the absolute z-position of a nanosphere can be determined through non-linear least squares (NLLS) fitting by measuring the fluorescence intensity at several different incidence angles.

Figure 2:
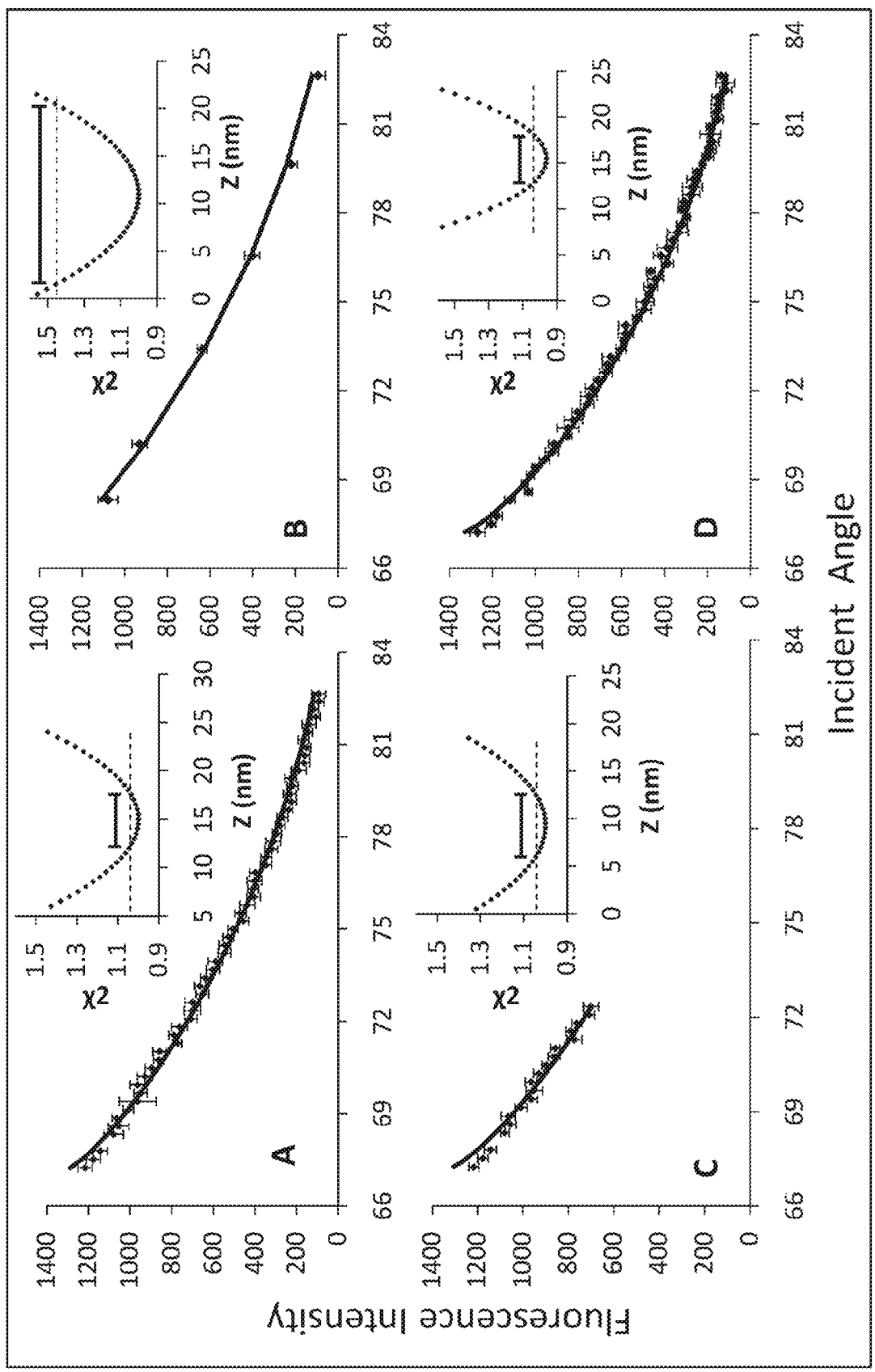
FIG. 2 is a set of graphs (A-D) illustrating experimental validation of the high resolution of 28 nanometer (nm) fluorescent nanospheres with the method and system of FIGS. 1A-D.

FIG. 2 graph A shows the fluorescence intensity profile of a 28-nm, dye-doped polystyrene nanosphere on the quartz prism/water interface at 60 different incident angles between 67.2° (the critical angle) and 82.6°. Each data point was the average of 5 measurements of the integrated fluorescence intensity of the whole particle subtracting the non-fluorescence background. The vertical center of the nanosphere was determined to be 15±2.8 nm by NLLS fittings using Equation 4, consistent with the geometrical center (14 nm or half of the diameter).

Theoretical and Experimental Analyses of Uncertainties in Vertical Position Determination.

It is important to note that there can be significant uncertainties in the z-values determined through NLLS fittings. Estimation of the uncertainties of the derived values in NLLS fittings is often ignored in the literature, yielding results of little statistical importance. Some literature report uncertainties based on asymptotic standard errors (ASEs) assumption, which usually underestimates the actual uncertainties in the recovered values.[19]

Here, we examined the confidence interval of the fitted z-values by support plane analysis[19] over the $\chi^2$-surface. $\chi^2$ is defined as:

$$\chi^2 = \sum_{1}^{m} \frac{1}{\sigma_m^2} [F_{exp} - F_{theor}]^2, \quad (5)$$

where $\sigma_m$ is the standard deviation obtained from m measurements at each incident angle; $F_{exp}$ and $F_{theor}$ are the experimental and theoretical fluorescence intensities, respectively. The detailed procedure to obtain the standard deviation of the axial position is to vary z close to its fitted value where $\chi^2$ reaches the global minimum, $\chi^2$(min). At each fixed z-value, the minimum $\chi^2$, $\chi^2$(par), is re-sought by floating the other parameter(s) (e.g., B in Equation 4). The confidence interval of z can then be estimated from $F_\chi$-statistic appropriate for p parameters and v degrees of freedom:

$$F_\chi = \frac{\chi^2(par)}{\chi^2(min)} = 1 + \frac{v}{p} F(p, v, P), \quad (6)$$

where P is the probability that the value of $F_\chi$ is due to random errors in the data. When P is smaller than 0.32, there is a 68% probability that the z-value yielding a corresponding $F_\chi$ is consistent with the experimental data, which is the usual definition of one standard deviation. For our measurements, $F_\chi$ with 2 parameters (p) and 60 degrees of freedom (v) with a probability (P) of 0.32 is 1.039. When $\chi^2$(par) is 1.039 times of $\chi^2$(min), the two corresponding z values are 12.3 and 17.8 nm, respectively (FIG. 2 graph A inset). Thus, the corresponding standard deviation for the fitted z is 2.8 nm, which results in an axial resolution of 8.4 nm, defined as 3 times the standard deviation. This precision in determining the axial resolution through a strict statistical analysis is so far the best in the literature.

There are two main features of our setup that allow us to reach this high precision. The first feature is the automatic calibration procedure to ensure the laser always illuminates the center of the field of view under a microscope. The second feature is the ability to scan through the widest range of incident angles in this prism-type TIRFM, which is especially important for large angles near 90°. These large angles are important in determining the z-positions and are usually unattainable in objective-type TIRFM. Furthermore, the incident angle intervals can be set at much smaller values than any existing TIRFM, thus leading to a larger number of data points for the NLLS fitting procedure.

To demonstrate the advantages of our setup, we show two examples of how these features contribute to the precision of the z-determination. The first example simulates a manual calibration/scan experiment with 6 data points that were arbitrarily chosen from the earlier data set and spanned the full range of angles. The calibration and measurement of fluorescence intensities at even only 6 incident angles can take hours if done manually. FIG. 2 graph B shows the NLLS fittings from these data points. The fitted z-value is 11±9.9 nm. The standard deviation was derived similarly through F-statistic analysis, with a $F_x$ value of 1.456 for 2 parameters and 6 degrees of freedoms. Note that the center of the nanosphere did not change much but the uncertainty of the z-value increased significantly, by a factor of 3.5 (FIG. 2 graph B inset). This is because the fitting results are more susceptible to noise when the number of data points is limited. It becomes apparent that it is advantageous to scan more angles to achieve better axial resolution.

We can also show that our new microscope is more advantageous than the commercially available objective-type TIRFM, which can be automated in calibration and scanning as well. However, one practical drawback of objective-type TIRFM is that the incident angle of the illumination beam is limited to a small range. Large incidence angles (approaching 90°) cannot be reached due to geometric constraints by the objective. FIG. 2 graph C shows that fluorescence intensities at these large angles are important in determining the z-positions in NLLS fittings. The data points used in the NLLS fittings were chosen from the same fluorescence intensity profile but with a limited range from the critical angle)(67.2° to the maximum angle that can be practically reached with objective-type TIRFM (72°).[13] The NLLS fittings are shown in FIG. 2 graph C and the fitted z-value is 9.3±3.1 nm. The center of the nanosphere changed much due to the sampling bias but the uncertainty of the z-value did not increase significantly, only by a factor of 1.1 (FIG. 2 graph C inset).

To examine the limit of the z-determination precision with angle-scanning TIRFM microscopy, we further studied the theoretical standard deviation through Monte Carlo simulation. The resolution is highly dependent upon the measurement errors of the fluorescence intensity at each incident angle. The standard deviation of fluorescence intensity measurement with 20 ms exposure time is relatively constant at 150 counts/frame/s, indicating the overall noise at this acquisition speed is dominated by the readout noise of the EMCCD camera. In the Monte Carlo simulation, when a flat noise at this level is added to the theoretical fluorescence intensity, the corresponding standard deviation for the fitted z-value is 2.0 nm, resulting in an axial resolution of 6.0 nm (FIG. 2 graph D). The theoretical resolution is only slightly better than our experimental value, which can be ascribed to the stability of the new instrument and the reproducibility of the calibration and scanning procedures.

Resolving Absolute z-Positions of Fluorescent Nanospheres Embedded in Agarose Gel.

In the literature, the axial position of a fluorescent object can also be calculated from[8]:

$$\Delta z = z_2 - z_1 = \ln \frac{F(z_1)}{F(z_2)}, \quad (7)$$

where $F(z_1)$ and $F(z_2)$ are the fluorescence intensities of a fluorescent object at positions $z_1$ and $z_2$, respectively. This method is usually used to dynamically track the z-positions of a particle. The best resolution of this method was reported to be 8 nm[8]. However, it should be noted that this method only reports the relative position difference in the axial direction ($\Delta z$). The initial absolute z value must be known to serve as the reference in order to find the following absolute positions. However, this criterion is usually difficult to meet in dynamic tracking experiments.

Figure 3:
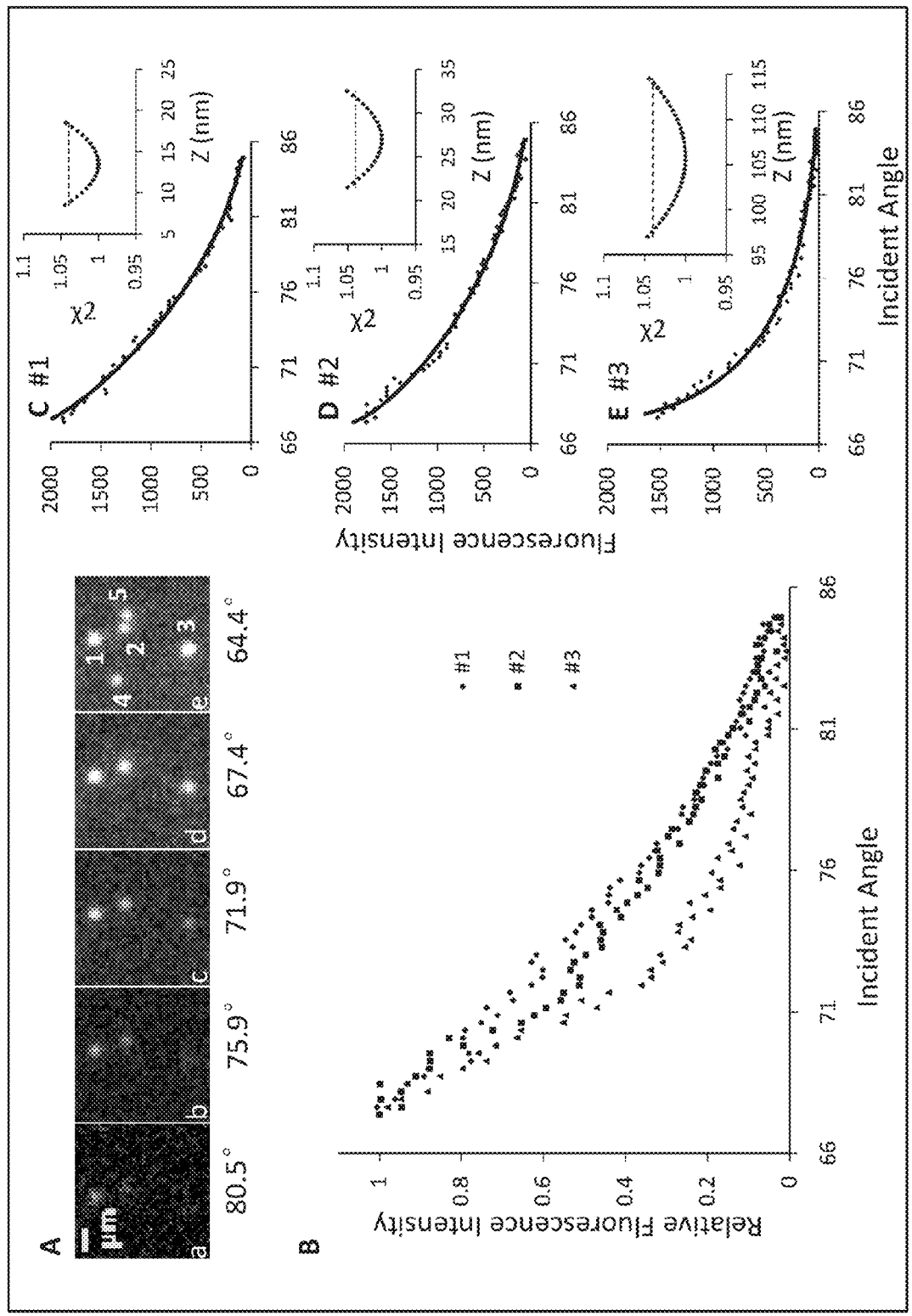
FIG. 3 is a set of recorded images (A) and correlated graphs (B-E) using the exemplary system, illustrating further experimental validation of resolution of fluorescent nanospheres at various light source incident angles with the method and system of FIGS. 1A-D.

To demonstrate that we are able to resolve the absolute z-distances of fluorescent objects with the new angle-scanning TIRFM, we buried fluorescent nanospheres in agarose gel and determined their z-distances from the TIR interface. The incident angle was varied to adjust the penetration depth of the EF, allowing the fluorescent particles to show up layer by layer. FIG. 3 images A shows 5 such particles that showed up sequentially as we scanned the incident angle from near 90° toward the critical angle. It is obvious that the relative vertical positions of the 3 particles labeled as 1, 2 and 3 have a relationship of $z_1<z_2<z_3$. Their absolute z-positions can be determined with NLLS fittings as described in the earlier section. FIG. 3 graph B shows different fluorescence intensity profiles as a function of incident angle for these three particles. The fitted axial positions are 18.5±4.5, 26.9±5.1 and 105.8±8.3 nm, respectively (FIG. 3 graphs C, D, E). The standard deviation increases along with the axial position, which is likely a result of decreased total fluorescence intensity as the particles are further away from the TIR interface.

Imaging Tilted Fluorescent Microtubules Buried in Agarose Gel.

Figure 4:
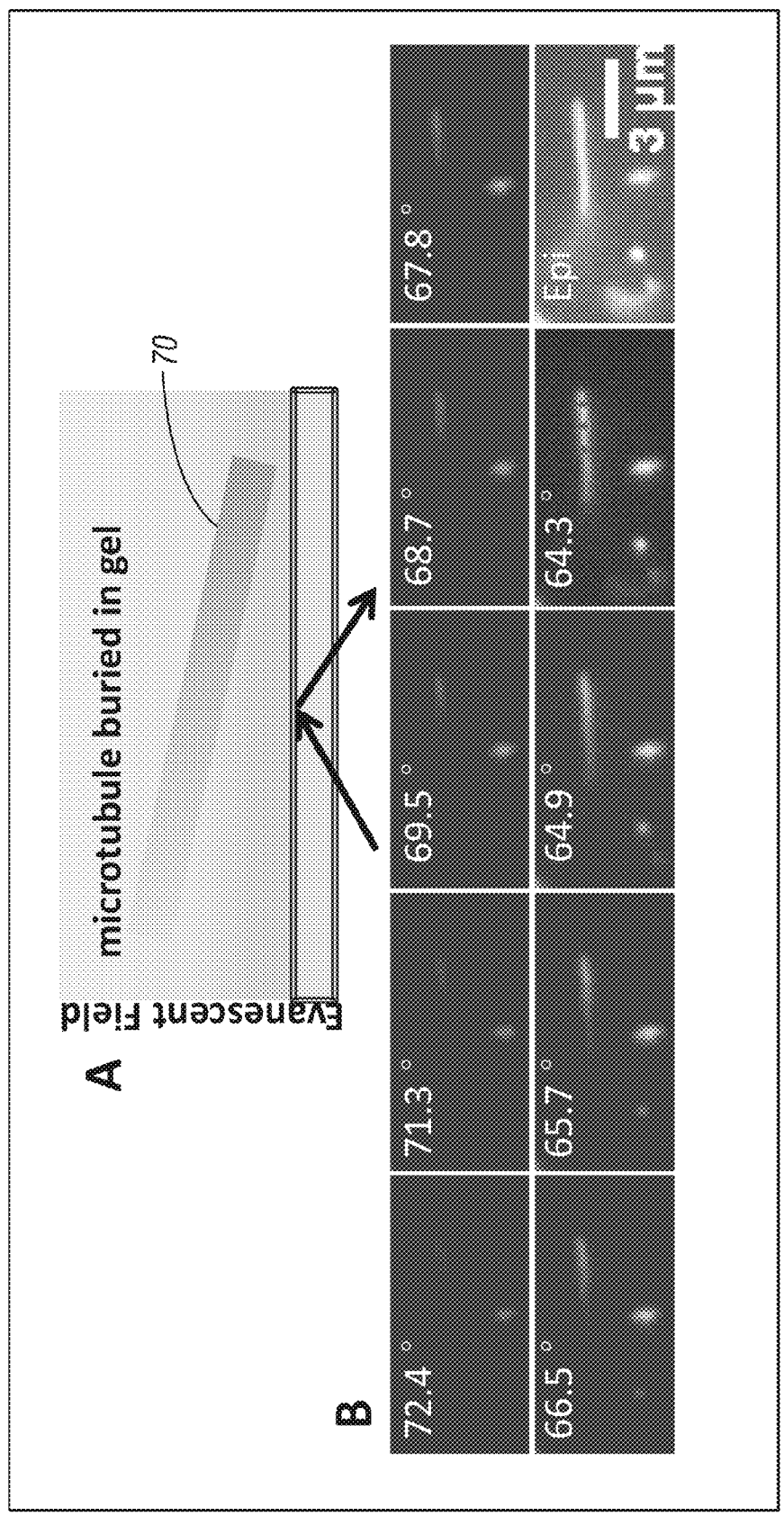
FIG. 4 illustrates one example of an application of the system of FIGS. 1A-D to imaging a microtubule, specifically a schematic diagram (A) and a set of actual microscopic images (B) of a microtubule buried in a gel imaged with the system of FIGS. 1A-D and illustrating resolution of the microtubule at various light source incident angles.

To further demonstrate the high vertical resolution of this setup, tilted microtubules buried in agarose gel were imaged. As shown in FIG. 4, the microtubules were illuminated section by section vertically using the new setup, while the whole microtubules were illuminated under epi-illumination. These images demonstrate that the particular microtubule did not lie horizontally flat in gel, but with a tilted angle. The depth differences of different parts in one single microtubule were resolved, and the tilting angle was calculated as demonstrated in FIG. 4.

Precise Surface Plasmon Resonance (SPR) Angle for Gold Metal Film Enhanced TIRFM.

TIRFM's high signal-to-noise ratio can be further improved through SPR by introducing a thin metal film, such as silver, aluminum or gold, on the sample slide. The incident angle that results in most significant fluorescence enhancement is referred to as the SPR angle. The enhancement effect drops sharply when the incident angle is deviated even slightly from the SPR angle, making it crucial to work at the exact SPR angle.[20] The SPR angle must be found experimentally, as the practical angle for a complex multi-layer interface often differs 1-2° from the theoretical value. However, finding the SPR angle manually is time consuming and labor intensive.

Figure 5:
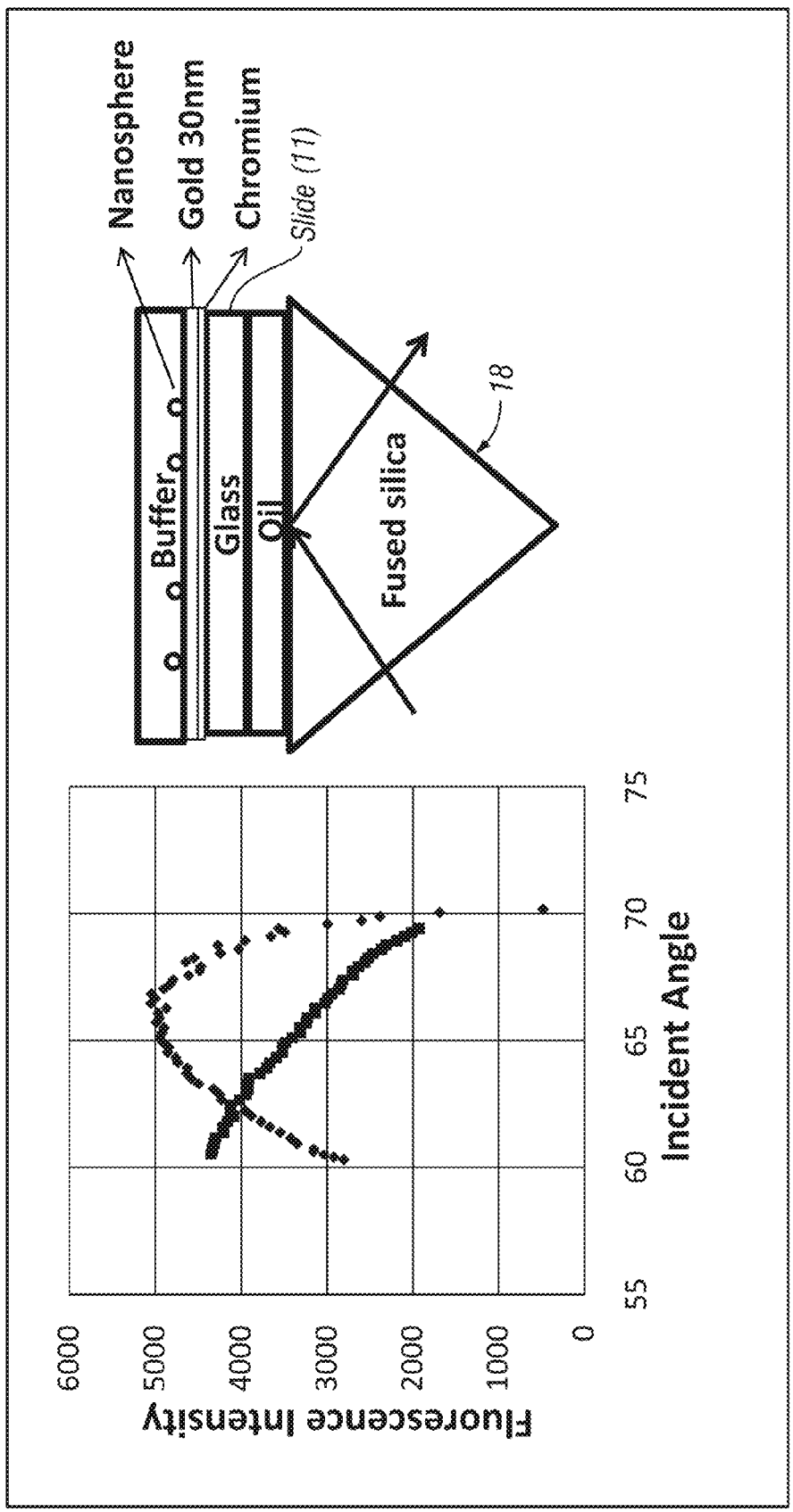
FIG. 5 illustrates another example of an application of the system of FIGS. 1A-D, namely a graph (left side) and correlated schematic diagram (right side) illustrating use of the system of FIGS. 1A-D to derive precise surface plasmon resonance (SPR) for gold film enhanced TIRFM.

Using the new setup, the SPR angle can be found much more quickly and accurately through automatic scanning and calibration in less than 2 mins. As shown in FIG. 5, the practical SPR angle was found to be 66.5° by scanning from 60.3° to 70.2° with an interval of 0.18°, which is much smaller than the intervals used in the previous reports.[21-22]

5. Conclusion Regarding Exemplary Embodiment One

An automatic calibration and angle-scanning TIRFM was built which can scan the full range of incident angles with increments smaller than 0.2°. The new instrument can provide axial resolution better than 10 nm. By using the instrument, the angle of a tilted microtubule in agarose gel was extracted, and the SPR angle of gold film enhanced TIRFM was found quickly and precisely.

The automation and precision of this new instrument makes it ideal for studies on systems with complex interfaces because the best illumination configuration can be found easily and reproducibly. For example, when TIRFM is used to study cell systems, the basal membrane at the sites where cells are attached to the substrate was imaged most of the time, while the apical membrane is rarely studied.[23] There are two main difficulties in adjusting the incident angle to let TIR occur in the apical interface: the difference between the refractive indices of the cytoplasm and the culture medium is too slight, and the apical membrane is not flat. The problem can be overcome with this new instrument by automatically scanning through a range of incident angles with very small increments. Additionally, when the incident angle is changed within the subcritical angle range, the instrument can be further applied to variable-angle epifluorescence. [24]

As can be seen by the foregoing detailed description and FIGS. 2-5 of the Exemplary Embodiment One, the improvements of the method and system have been validated. Improved axial resolution is a result.

6. References Regarding Exemplary Embodiment One

1. D. Axelrod, in *Biophysical Tools for Biologists, Volume Two: In Vivo Techniques*, ed. J. J. Correia, H. W. Detrich. Academic Press, 1 edn., 2008, vol. 89, pp 169-221.
2. X. H. Xu, E. S. Yeung, *Science* 1997, 275. 1106-1109.
3. X. H. N. Xu, E. S. Yeung, *Science* 1998, 281. 1650-1653.
4. Y. He, H. W. Li, E. S. Yeung, *J. Phys. Chem. B* 2005, 109. 8820-8832.
5. S. H. Kang, M. R. Shortreed, E. S. Yeung, *Anal. Chem.* 2001, 73. 1091-1099.
6. S. H. Kang, E. S. Yeung, *Anal. Chem.* 2002, 74. 6334-6339.
7. Sarkar, R. B. Robertson, J. M. Fernandez, *PNAS* 2004, 101. 12882-12886.
8. S. Saffarian, T. Kirchhausen, *Biophys. J.* 2008, 94. 2333-2342.
9. M. Oheim, D. Loerke, W. Stuhmer, R. H. Chow, *Eur. Biophys. J.* 1998, 27.83-98.
10. J. A. Steyer, W. Almers, *Biophys. J.* 1999, 76. 2262-2271.
11. L. Mattheyses, D. Axelrod, *Journal of Biomedical Optics* 2006, 11.7.
12. P. Olveczky, N. Periasamy, A. S. Verkman, *Biophys. J.* 1997, 73. 2836-2847.
13. Gell, M. Berndt, J. Enderlein, S. Diez, *J. Microsc. (Oxford)* 2009, 234.38-46.
14. G. M. Omann, D. Axelrod, *Biophys. J.* 1996, 71. 2885-2891.
15. C. J. Merrifield, M. E. Feldman, L. Wan, W. Almers, *Nat. Cell Biol.* 2002, 4. 691-698.
16. F. Lanni, A. S. Waggoner, D. L. Taylor, *Journal of Cell Biology* 1985, 100. 1091-1102.
17. D. Loerke, W. Stuhmer, M. Oheim, *J. Neurosci. Methods* 2002, 119.65-73.
18. Rohrbach, *Biophys. J.* 2000, 78. 2641-2654.
19. J. R. Lakowicz, *Principles of Fluorescence Spectroscopy* 3$^{rd}$ ed.; Springer: 2006.
20. T. P. Burghardt, J. E. Charlesworth, M. F. Halstead, J. E. Tarara, K. Ajtai, *Biophys. J.* 2006, 90. 4662-4671.
21. E. G. Matveeva, I. Gryczynski, A. Barnett, N. Calander, Z. Gryczynski, *Anal. Bioanal. Chem.* 2007, 388. 1127-1135.
22. J. Borejdo, Z. Gryczynski, N. Calander, P. Muthu, I. Gryczynski, *Biophys. J.* 2006, 91. 2626-2635.
23. Y. Sako, S. Minoghchi, T. Yanagida, *Nat. Cell Biol.* 2000, 2.168-172.
24. C. A. Konopka, S. Y. Bednarek, *Plant J.* 2008, 53.186-196.

7. Figure Captions for Embodiment One

FIG. 1A. Schematic experimental setup for two color automatic angle scanning prism type total internal reflection fluorescence microscopy (TIRFM). M, mirror; S, mechanical shutter; FL, focusing lens.

FIG. 2. Non-linear least squares (NLLS) fittings for the axial positions of 28-nm fluorescent nanospheres according to their fluorescence intensity profiles as a function of incidence angle. The solid dots are the average fluorescence intensities at 60 different incident angles ranging from 67.2° (the critical angle) to 82.6° and the red curves are the NLLS fitting with Equation 4. Each dashed horizontal line on the $\chi^2$-surface (the insets) indicates the threshold at which there is a 68% probability that the corresponding z-value is consistent with the experimental data. (A) The fitting from the whole data set consisting of 60 angles ranging from 67.2° (the critical angle) to 82.6° degrees. (B) The fitting from a subset containing 6 data points to simulate a manual scanning experiment. (C) The fitting from a subset that spans from 67.2° (the critical angle) to 72° to simulate an objective-type TIRFM experiment. (D) The fitting from Monte Carlo simulation.

FIG. 3. Fluorescent nanospheres imbedded in agarose gel. (A) Five nanospheres illuminated at the incident angles of 80.5° (a), 75.9° (b), 71.9° (c), the critical angle 67.4° (d), and 64.4° (e (B). The fluorescence intensity profiles of particles 1, 2 and 3 as a function of incident angle. Each curve was normalized to the intensity at the critical angle. (C), (D) and (E) are the NLLS fittings according to Equation 4. The insets show the one time of the standard deviation of the NLLS fittings.

FIG. 4. Tilted fluorescent microtubules in agarose gel. (A) The schematic position of the tilted microtubule in agarose gel. (B) The fluorescence images at different incident angles. Three positions on the same microtubule (marked by stars *), which were equally spaced 635 nm apart in the horizontal direction, were chosen to analyze their axial positions (see image labeled "64.3°"). Through fitting their fluorescence intensity decay curve, their vertical positions were extracted as: 75.1 nm, 125.9 nm, and 176.3 nm, respectively. Therefore, the titling angle of the microtubule was 4.6°.

FIG. 5. SPR angle for gold film enhanced TIRFM, which is illustrated in the cartoon. The (diamond shapes) curve with a peak was generated from gold film enhanced TIRFM, and the incident angle at the peak position was 66.5°. The curve without an obvious peak was created without the gold film coating.

FIG. 5. SPR angle for gold film enhanced TIRFM, which is illustrated in the cartoon. The blue curve with a peak was generated from gold film enhanced TIRFM, and the incident angle at the peak position was 66.5°. The curve without an obvious peak was created without the gold film coating.

C. Exemplary Embodiment Two

1. Overview of Exemplary Embodiment Two

An automatic calibration and angle-scanning prism-type total internal reflection fluorescence microscope (TIRFM) (e.g. like embodiment one described above) was modified to function in both TIRFM and pseudo TIRFM modes. When the incident angle of the excitation laser beam was controlled to be larger than the critical angle, the instrument served as a variable-angle TIRFM. A computer program automatically calibrates the laser illumination spot in the sample to overlap with the center of the microscope's field of view. Then by measuring the fluorescence intensities at different incident angles, the z-positions of fluorescent nanospheres close to the cell basolateral membrane can be extracted. When the incident angle is reduced to be in the subcritical range, the instrument works as a pseudo TIRFM. The whole cell body from bottom to top can be imaged in a vertical scan process. Furthermore, the illumination field depth in the pseudo TIRFM can be controlled through changing the incident angle or the horizontal position of the laser spot.

A large number of biological events take place inside a living cell at any moment to keep the cell functioning properly. To have a better understanding of these biological phenomena, researchers have taken great efforts in developing a variety of imaging tools, such as epi-fluorescence, confocal fluorescence and total internal reflection fluorescence (TIRFM) microscopies,[1-3] for specific fluorescent labeling of proteins in both fixed and live cells.[4] Because of the native thin evanescent field, the background noise in TIRFM is much lower than that in epi-fluorescence microscopy.[2,5] Additionally, unlike confocal fluorescence microscopy, TIRFM has better z-resolution and does not require a pinhole in the back focal plane of the objective to block the light leaking from out-of-focus planes. TIRFM has become an indispensable tool to study cellular organization and dynamic processes that occur near the interface of cell culture and glass substrate.[6]

In embodiment one described earlier,[7] an auto-calibration variable-angle prism-type TIRFM setup was introduced and demonstrated to have a better practical resolution in the axial direction than any other existing variable-angle TIRFM system. An optimized system layout and an automatic high-precision calibration procedure were implemented to find the incident angles with intervals smaller than 0.2° reliably and reproducibly within minutes. Furthermore, it becomes possible to scan the widest range of incident angles from the critical angle to large angles near 90°. A larger number of data points can be collected for a better practical resolution in the axial direction. The large angles that are unattainable in objective-type TIRFM are important in determining the absolute z-positions.

Because the evanescent field is no more than a few hundred nanometers thick, TIRFM is mostly used to study dynamic processes that occur near the basolateral membrane of mammalian cells. However, these dynamic processes often continue beyond the evanescent field. For example, using TIRFM alone is impossible to answer the question about how vesicles formed during endocytosis move away from the membrane towards cell nuclear or other organelles. Another example of TIRFM's limitation in imaging depth is its inability in studies of plant cells.[8] It is difficult for the evanescent wave to penetrate the plant cell wall, because the thickness of the cell wall is usually several hundred nanometers or more, and plant cells often do not lie flat on the substrate. To help solve these technical problems, variable angle epi-fluorescence or pseudo TIRFM[8] was designed to work at subcritical angles that are smaller than yet still close to the critical angle. At a subcritical incident angle, the excitation laser beam is refracted to produce a slanted illumination path; thus, it is possible to extend the illumination depth several micrometers into the cell body.

In embodiment two, we demonstrate a new microscope system that combines the variable-angle TIRFM and variable-illumination-depth pseudo TIRFM to image the whole cell from the basolateral membrane to the apical membrane. The illumination depth of the slanted refracted light just below the objective lens was regulated by varying the horizontal position of the laser spot at the interface of cell culture and glass substrate, or by adjusting the incident angle.

2. Instrumentation

Figure 6:
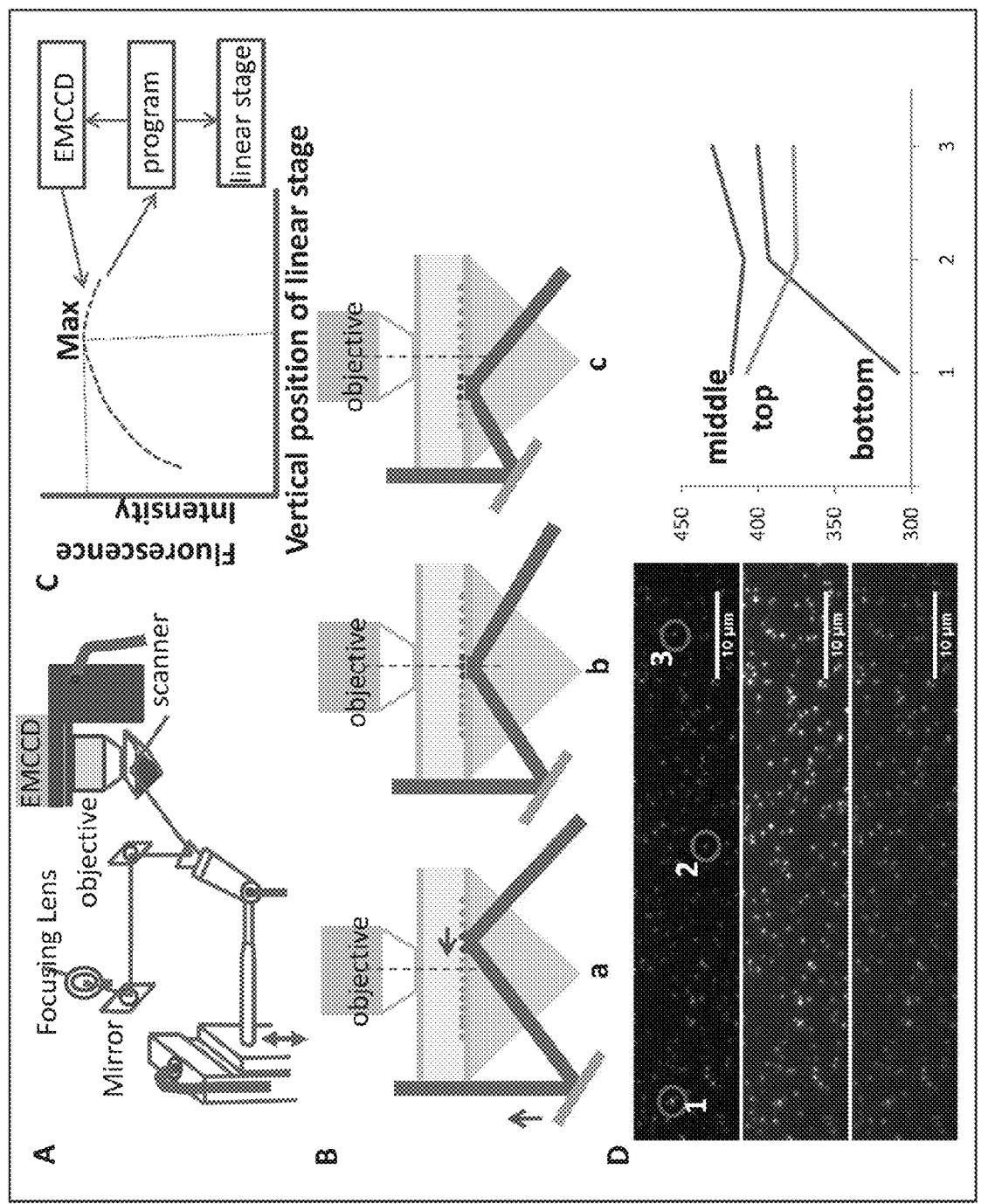
FIG. 6 is another schematic of a TIRFM set up and angle scan process according to the invention.

The apparatus used was similar to that described previously in embodiment one,[7] except for one modification: a piezo-actuated z-scanner (P-721, Physik Instrumente, Germany) was coupled to the microscope objective (FIG. 6, schematic A). The scanner offers the ability to change the vertical position of objective's front focal plane with very high precision. Additionally, when observing the cell structures in bright-field microscopy, the laser for TIRFM was turned off and the illumination light source of the microscope was turned on.

The field of view of under the 100× objective was around 130×130 μm². If the illumination spot is too large, less energy can be used to excite the sample in field of view; if the spot is too small, the laser spot may not fully cover the field of view, and the Gaussian shaped energy distribution could lead to an annoying uneven illumination in the field of view. It was found that when the diameter of the illumination laser spot was adjusted to be around 150 μm by controlling the relative distance between the focusing lens and the prism, the optimized laser energy distribution and sample illumination in the field of view was obtained.

A computer program (implemented through the user interface shown in FIG. 7) was developed to automatically optimize the horizontal position of the laser spot at each incident angle. After the user enters an incident angle range, this computer program carries out the auto-calibration in two rounds: rough scan and fine-tune. To maintain high precision, the motorized linear stage travels step by step in only one direction. The fluorescence images are recorded by the EMCCD camera at each step. During the rough scan, the vertical step size is set to be relatively large to reduce the time required for a full scan, and the vertical positions of the mirror of galvanometer at all incident angles are obtained from each local maximum of the integrated fluorescence intensities in a chosen area.

FIG. 6 shows the details of the scan process. When the incident angle is set at a large value, the laser spot on the prism surface is to the right of microscope objective lens (FIG. 6, schematic B-a). Then the program moves the linear vertical stage upwards. The higher the stage gets, the more to the left the laser spot on the prism surface moves. At the same time, the program utilizes the EMCCD to record fluorescence images and calculate intensities. The collected fluorescence intensity at a given incident angle depends on the horizontal position of the laser spot on the prism surface. The program keeps moving the linear stage up until the laser spot passes the center of the objective lens (FIG. 6, schematic B-b) and reaches a position slightly to the left of the objective lens (FIG. 6, schematic B-C). The recorded intensity changing profile (FIG. 6, schematic C) is sent to the program as feedback to find the calibrated vertical position of the linear stage. All of the incident angles based on the user-defined range and interval are "roughly" calibrated in a continuous scan process.

During the round of fine-tune, the program controls the linear vertical stage to move around the "roughly-calibrated" positions again but with a smaller step size to obtain more precise vertical positions. Only when the center of the laser spot overlaps perfectly with the center of the objective lens, the fluorescence intensity is at the highest level (FIG. 6, illustration D). Multiple rounds of fine-tune can be carried out if desired. The angles and vertical positions are recorded and can be reloaded when starting new experiments.

Increasing fluorescence intensities of fluorescent nanospheres (28 nm) immobilized on the prism surface has been demonstrated when the incident angle was scanned from 82.6° to 67.2° in TIRFM. The total number of angles scanned was 64, the exposure time for each angle was 50 ms, and it took ~15 s to complete the whole scan process. During the scan process, it took a fraction of a second up to a few seconds for the linear vertical stage to travel to the right position for the next incident angle, which accounts for the extra 12 s in addition to the total exposure time for the whole scan process. To avoid photo-bleaching during the scan process, the computer program was designed to open the shutter only when the EMCCD camera is required to collect fluorescence signals. By using a high-speed motorized stage, the time required to perform a full scan can be further reduced.

Sample Preparation

Preparation of Coverslips Coated with Metal Films.

Figure 8:
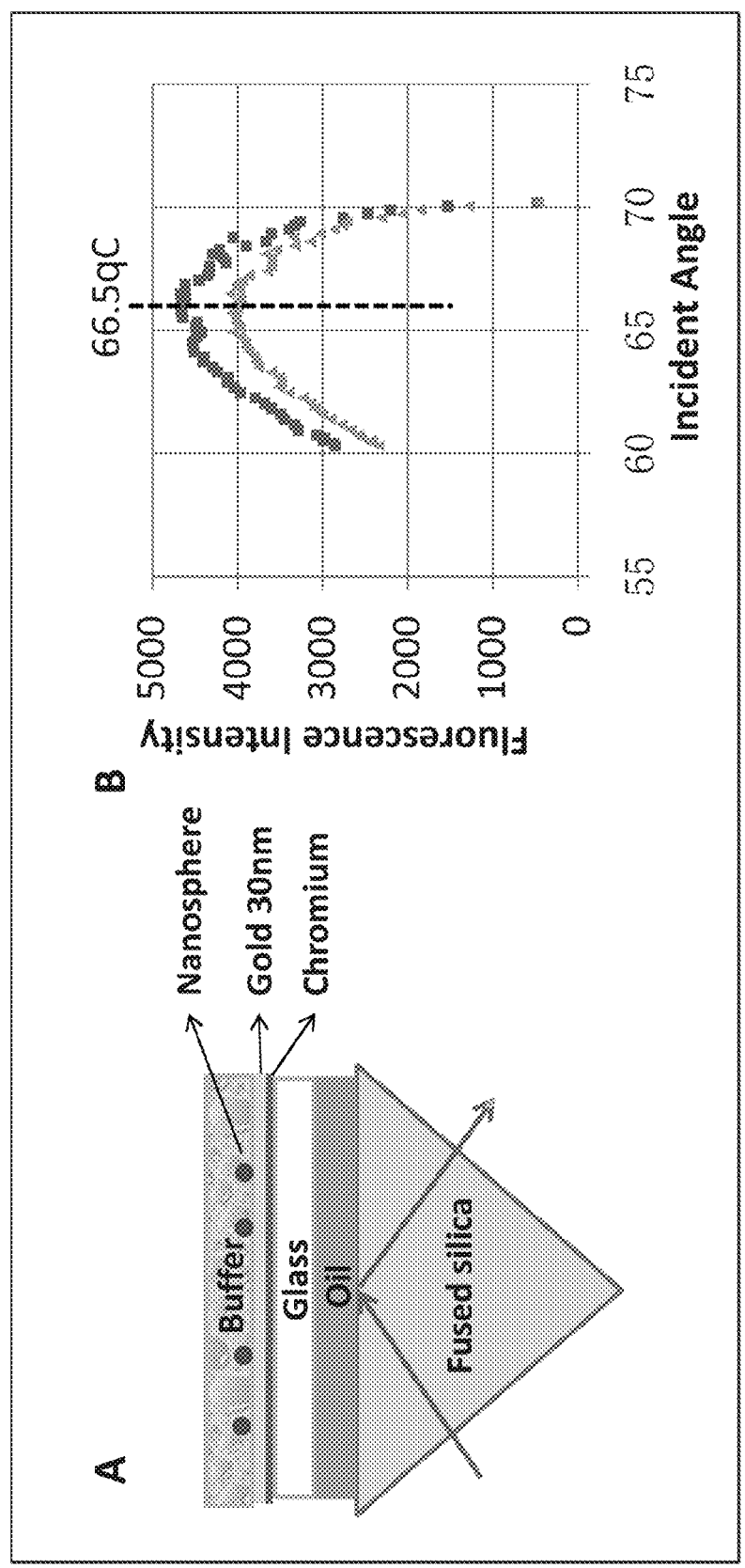
FIG. 8 are illustrations, photos, and graphs illustrating schematically gold film enhanced TIRFM and fluorescence intensity curves for a nanosphere therein according to another embodiment.

Thoroughly cleaned coverslips (22 mm×22 mm, Zinc Titania glass, refractive index 1.523 at sodium D line, Corning, N.Y.) were deposited with 5 nm of chromium followed by 30 nm of gold in an Airco Temscal BJD1800 E-beam evaporator (Berkeley, Calif.). Then the coverslips were coated with poly-L-lysine (PLL) to form positively charged surfaces. Negatively charged 28-nm diameter fluorescent nanospheres (Duke Scientific, Palo Alto, Calif.) were diluted to proper concentration in 18.2 MΩ water containing an oxygen scavenging system, composed of 0.5 mg/ml glucose oxidase (Sigma), 40 µg/ml catalase (Sigma), 10% (w/v) glucose (Sigma) and 1% (v/v) β-mercaptoethanol (Fluka). The nanosphere solution was then loaded on a PLL-modified gold-coated coverslip and covered with another clean coverslip. The sample slide was placed on the prism surface. When imaging, a set of one 532-nm longpass filter and one 620/60 nm bandpass filter (Chroma, Rockingham, Vt.) was put between the EMCCD camera and the microscope to filter away the excitation background from the emission fluorescence. FIG. 8 illustrates an example of gold-enhanced TIRFM set up and intensity curves for the same nanosphere.

Preparation of Cell Samples on Coverslips.

A549 Human lung cancer cells (CCL-185, ATCC, Manassas, Va.) were cultured in T-25 flasks with minimum essential medium containing 10% fetal bovine serum. When sub-culturing, the cells were seeded on poly-1-lysine (PLL) coated coverslip and grew in 37° C. incubator with 5% $CO_2$ atmosphere. After 24 hours, the cells were incubated in cell culture medium containing 100 nm diameter fluorescent nanospheres in the same 37° C. incubator. After that, the cells on coverslip were fixed with 3% formaldehyde and 0.1% glutaraldehyde in phosphate buffer at 37° C. for 15 min. Then the cells were immersed in phosphate buffer containing oxygen scavenging system composed of 0.5 mg/ml glucose oxidase (Sigma), 40 µg/ml catalase (Sigma), 10% (w/v) glucose (Sigma) and 1% (v/v) β-mercaptoethanol (Fluka). The oxygen scavenging system helped to reduce photo-bleaching. Finally, the coverslip was put on the TIRFM prism surface for imaging. The same set of filters used above was put between the EMCCD camera and the microscope.

Precision and Reproducibility of Instrument

To demonstrate the system's precision and reproducibility, the new microscope was used to find the exact incident surface plasmon resonance (SPR) angle that produced the most intense evanescent field for metal enhanced TIRFM with a p-polarized (in the plane of incidence formed by the incident and reflected beams) incident laser beam as the illumination light. Two independent runs of the same experiment were carried out. The incident angles at the peak positions for the 2 curves were nearly identical at 66.5°. The intensity differences between the 2 curves were mainly resulted from the slight photo-bleaching of the fluorescent beads.

Cell Imaging

Figure 9:
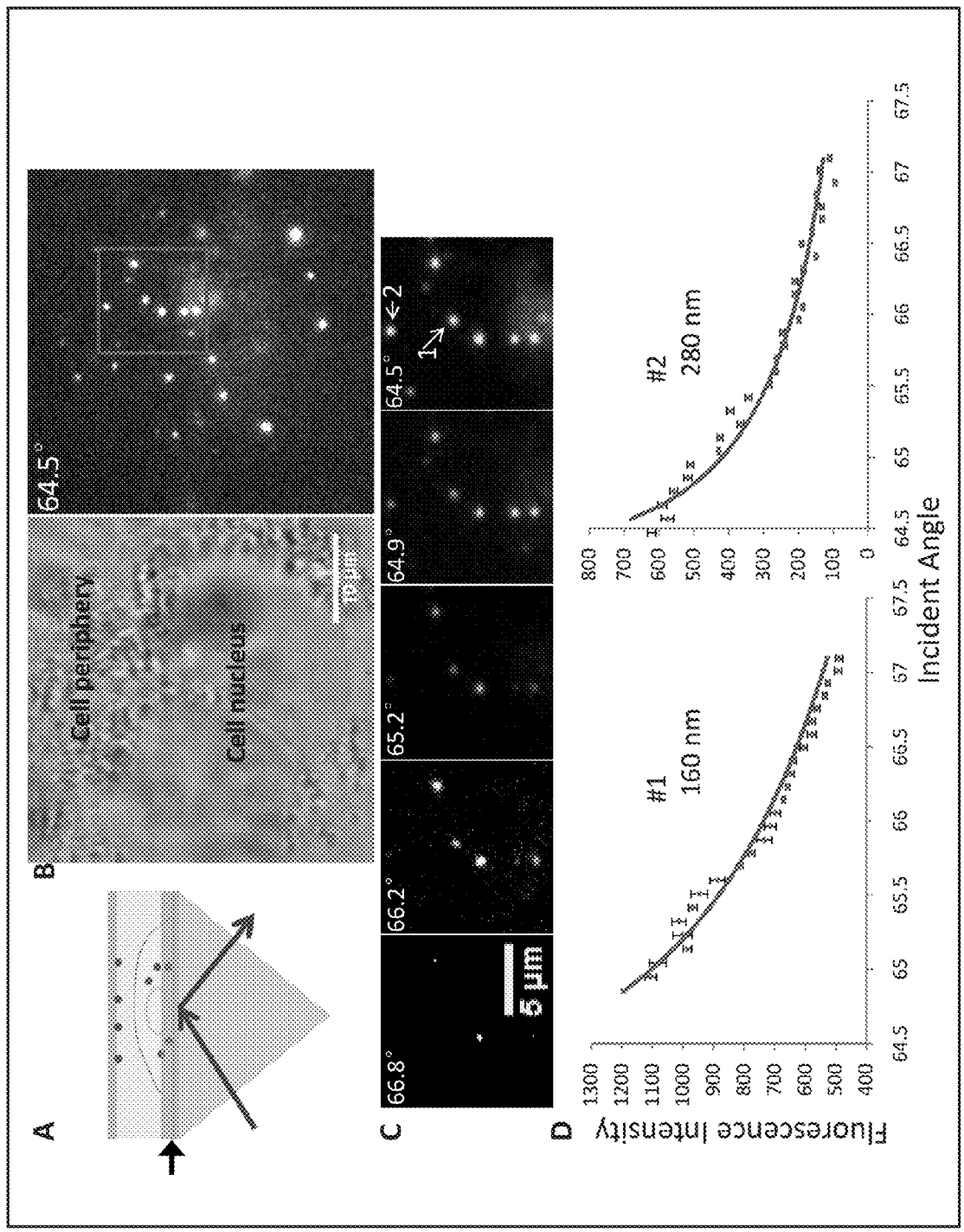
FIG. 9 are micrograph photos, fluorescence curves, and a schematic of another VA-TIRFM example.

Determination of Z-Positions of Fluorescent Nanospheres in Cell Basolateral Part with Variable-Angle TIRFM The incident angle of the laser beam was first set to be greater than the critical angle so that the instrument functioned as a TIRFM. The incident angle was varied to adjust the penetration depth of the evanescent wave, allowing the fluorescent nanospheres to show up layer by layer (FIG. 9). These fluorescent nanospheres were distributed in the cell basolateral part which was within several hundred nanometers from the interface of cell culture and glass substrate.

The absolute z-positions of these fluorescent particles can be extracted with the method of NLLS fitting as described with embodiment one.[7] FIG. 9, graphs D1 and D2 show fluorescence intensity profile of a chosen nanosphere varies as a function of the incident angle:

$$F(\theta) = A\cos^2\theta e^{-z/d(\theta)}, \quad (1)$$

where $F(\theta)$ is the collected fluorescence intensity; $\theta$ is the incident angle; A is the instrument constant; z is the absolute vertical position of the chosen fluorescent nanosphere; $d(\theta)$ is the penetration depth which is defined by the following equation:

$$d(\theta) = \frac{\lambda}{4\pi\sqrt{(n_1\sin\theta)^2 - n_2^2}}, \quad (2)$$

where $\lambda$ is the wavelength of the incident light; $n_1$ and $n_2$ are the high and low refractive indices of the two media at the interface. By fitting the fluorescence decay curves with Equation 1, the absolute z-positions of the two particles are calculated to be $z_1=160$ nm and $z_2=280$ nm, respectively (FIG. 9, graphs D1 and D2). The fitting result is consistent with the experimental observation: particle 1 appeared earlier than particle 2 when the incident angle was scanned from large value (66.8°) to small value (64.5°).

Imaging Fluorescent Nanospheres Distributed Deeper Inside the Cell with Variable-Illumination-Depth Pseudo TIRFM The instrument functions as a pseudo TIRFM when the incident angle is within the subcritical angle range, that is, a few degrees smaller than the critical angle. The refracted light instead of the evanescent wave penetrates into the cell body and the illumination field depth (the slanted illumination path above the cell culture and glass substrate interface) changes from several hundred nanometers to several micrometers. The narrow subcritical angle range maintains the illumination field close to the substrate, thus providing reasonable signal to noise ratios by keeping the background noise at a low level.

Unlike TIRFM, pseudo TIRFM does not require the center of the laser spot at the cell/glass interface to overlap with the center of the objective lens. When the laser spot is moved away from the center of the objective lens, the refracted laser beam can effectively illuminate much deeper into the cell body.

Figure 10:
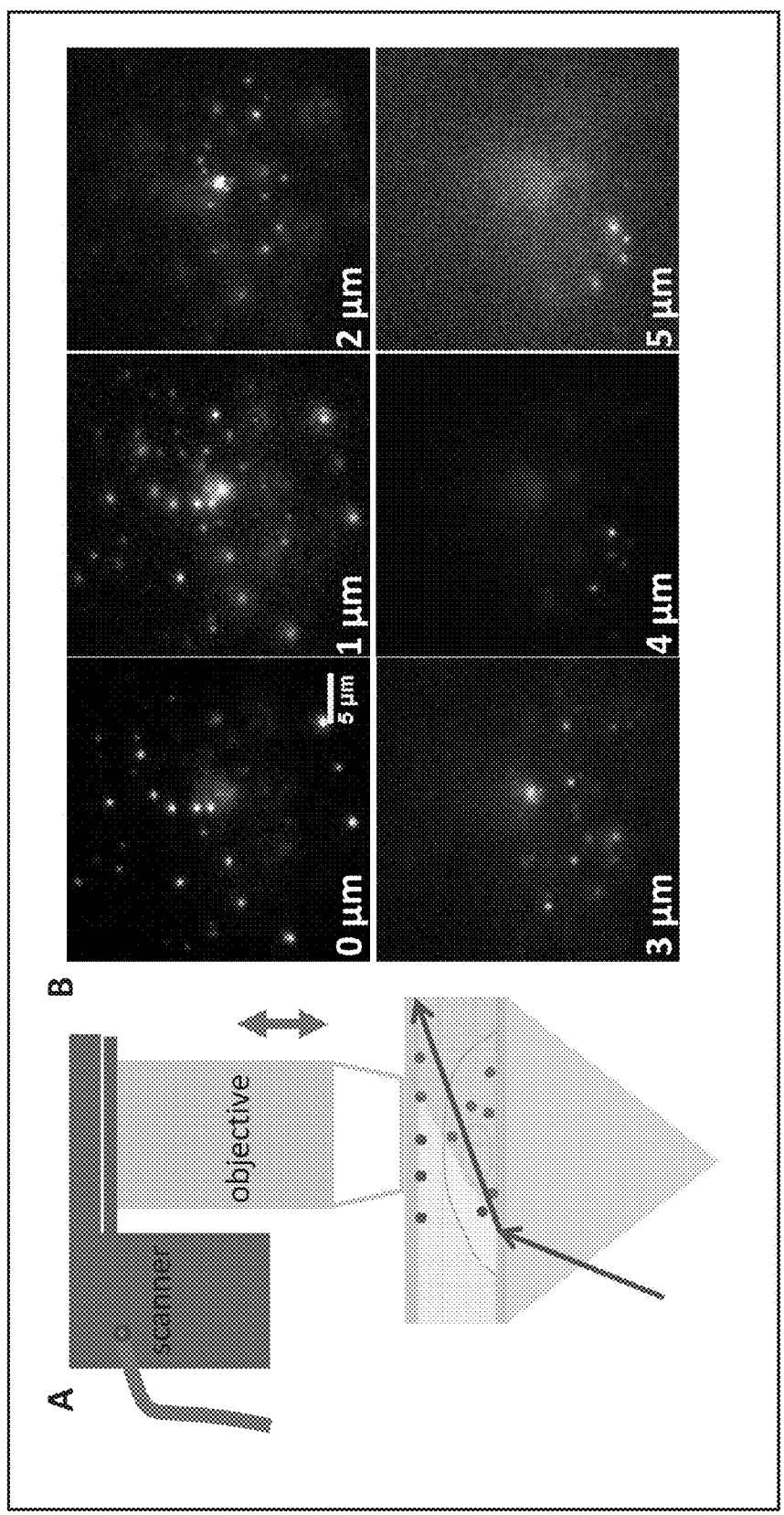
FIG. 10 are micrographs and illustrations of aspects of an embodiment two pseudo TIRFM examples.

The micrographs in FIG. 10 were taken at the incident angle of 63.5°, less than 1° smaller than the critical angle of 64.4°. The objective's focal plane was scanned from bottom to top through the whole cell body of about 5 µm thick. When the focal plane was set to the cell/glass interface, the fluorescent nanospheres located within the evanescent field of TIRFM could still be detected in pseudo TIRFM with good signal to noise ratios. Then the objective's focal plane was moved away from the interface while the excitation conditions remained constant. More fluorescent nanospheres located deeper inside the cell became detectable layer by layer. Thus, fluorescent nanospheres at different depths inside the whole cell body were imaged.

To selectively image fluorescent nanospheres within a certain depth inside the cell body, the depth of the illumination field just below the objective lens can be adjusted by changing either the incident angle in the subcritical angle range or the horizontal position of the excitation laser spot at the interface of cell culture and glass substrate. These procedures are demonstrated in FIG. 11. Changing incident angle is the only way for objective-type pseudo TIRFM to adjust the illumination depth, while this prism-type system provides one more option.

Conclusion Re Embodiment Two

A new microscope that can function as either a variable-angle TIRFM or variable-illumination-depth pseudo TIRFM was built. Fluorescent nanospheres close to the cell basolateral membrane are illuminated when the system functions as a variable-angle TIRFM. When the system functions as a pseudo TIRFM, the whole cell, including the cell basolateral membrane, can be illuminated. Furthermore, by changing the incident angle or adjusting the horizontal position of the laser spot in the cell culture and glass substrate interface, fluorescent nanospheres with different vertical positions inside the whole cell body can be selectively imaged. This new automated microscope system provides a reliable, reproducible way to study biological events inside the cell.

References Re Embodiment Two (1) Holz, R. W.; Axelrod, D. Secretory granule behaviour adjacent to the plasma membrane before and during exocytosis: total internal reflection fluorescence microscopy studies. *Acta Physiol.* 2008, 192, 303.
(2) Axelrod, D. Total Internal Reflection Fluorescence Microscopy. In *Biophysical Tools for Biologists, Volume Two: In Vivo Techniques*; 1 ed.; Correia, J. J., Detrich, H. W., Eds.; Academic Press: 2008; Vol. 89, p 169.
(3) Axelrod, D.; Omann, G. M. Combinatorial microscopy. *Nat. Rev. Mol. Cell. Biol.* 2006, 7, 944.
(4) Chen, I.; Ting, A. Y. Site-specific labeling of proteins with small molecules in live cells. *Curr. Opin. Biotechnol.* 2005, 16, 35.
(5) Lang, E.; Baier, J.; Kohler, J. Epifluorescence, confocal and total internal reflection microscopy for single-molecule experiments: a quantitative comparison. *J. Microsc.-Oxf.* 2006, 222, 118.
(6) Wazawa, T.; Ueda, M. Total internal reflection fluorescence microscopy in single molecule nanobioscience. In *Microscopy Techniques*; Springer-Verlag Berlin: Berlin, 2005; Vol. 95, p 77.
(7) Sun, W.; Marchuk, K.; Wang, G. F.; Fang, N. Autocalibrated Scanning-Angle Prism-Type Total Internal Reflection Fluorescence Microscopy for Nanometer-Precision Axial Position determination. *Anal. Chem.,* 82, 2441.
(8) Konopka, C. A.; Bednarek, S. Y. Variable-angle epifluorescence microscopy: a new way to look at protein dynamics in the plant cell cortex. *Plant J.* 2008, 53, 186.

Figure Captions Re Embodiment Two

FIG. 6. Schematic experimental setup and the angle scan process for TIRFM. (A) Schematic experimental setup for automatic angle scanning prism-type TIRFM. The two light paths are symmetrical at the two sides of the prism. (B) The rough angle scan process at a given incident angle. The red dots are fluorescent nanospheres distributed on the prism surface. (C) The flow chart to show how the home-made program carries out the angle scan process. (D) Experimental images of the fine-tune process. Top micrograph: the illumination laser spot was to the left of the field of view; middle micrograph: the illumination laser spot overlapped with the center of field of view; bottom micrograph: the illumination laser spot is to the right of the field of view. The right chart is the intensities of 3 chosen fluorescent nanospheres for the 3 left micrographs. The x-axis shows the 3 nanospheres, and the y-axis is the fluorescence intensity.

Figure 7:
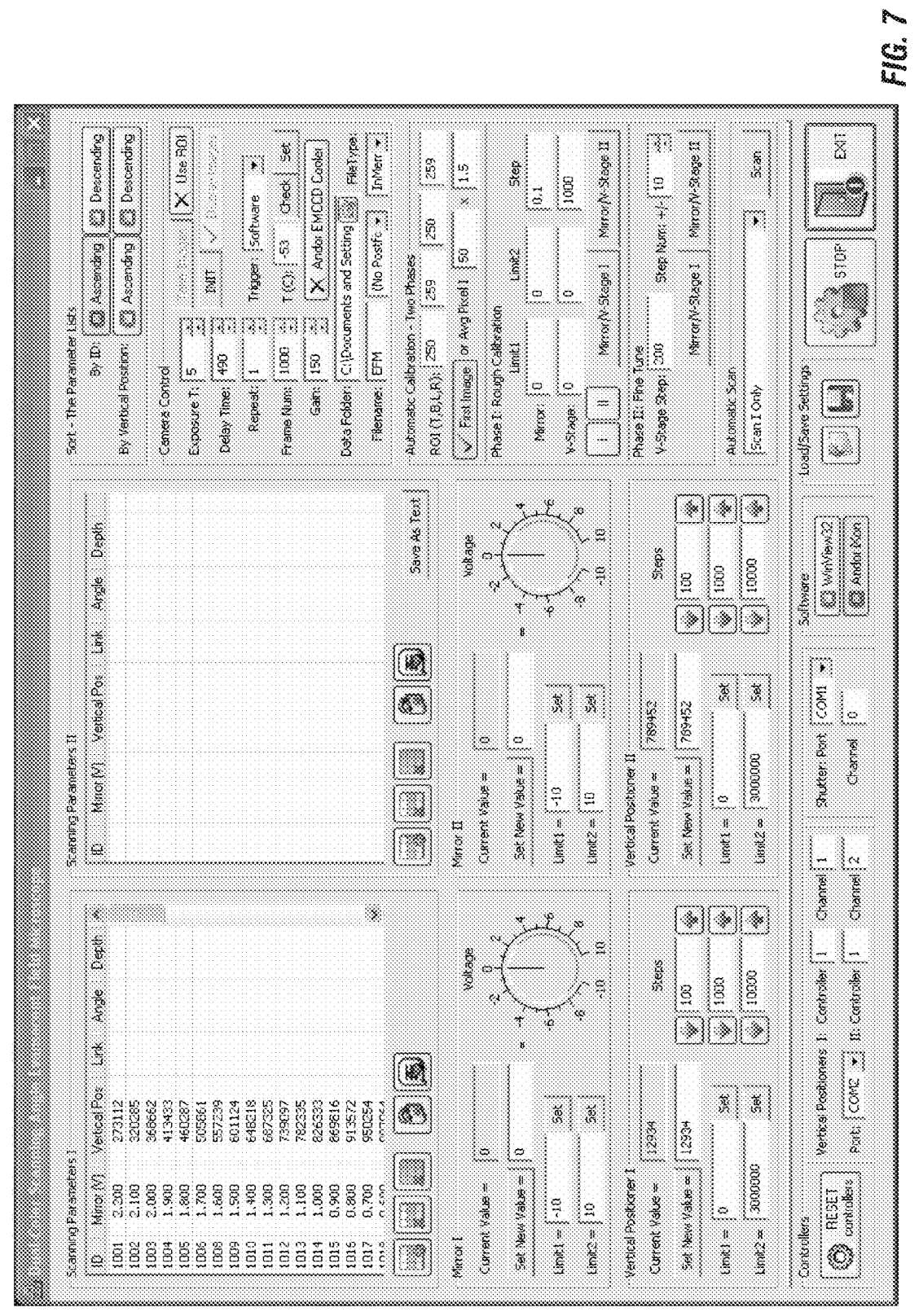

FIG. 7. The user interface of the auto-calibration auto-scanning program.

FIG. 8. SPR angle for gold film enhanced TIRFM. (A) An illustration of the sample and imaging setup. (B) Two fluorescence intensity curves of the same nanosphere. The 2 curves were generated from two independent runs of the same experiment. The top curve is the $1^{st}$ run.

FIG. 9. Fluorescent nanospheres distributed close to the cell basolateral membrane were imaged by variable-angle TIRFM. (A) Schematic diagram showing the cell imaged within the evanescent field. The interface of cell culture and glass substrate is pointed out by the black arrow. (B) An A549 cell imaged in bright-field microscopy and TIRFM at an incident angle of 64.5°. The image areas are identical. (C) The TIRFM micrographs of the area defined by the red square in (B). The incident angles are shown at the top-left corner of these micrographs. It is obvious that the relative vertical positions of the two particles labeled as 1 and 2 have a relationship of $z_1<z_2$. (D) Fluorescence decay curves of the two labeled nanospheres. The NLLS fitting curves are shown in red.

FIG. 10. Whole cell scanned in pseudo TIRF. (A) Schematic diagram of pseudo TIRFM. The objective's focal plane was adjusted by the objective scanner. (B) Images of cell areas at different vertical depth. The cell was scanned from the basolateral membrane to the apical membrane with 1 μm interval. The whole cell thickness was around 5 μm.

Figure 11:
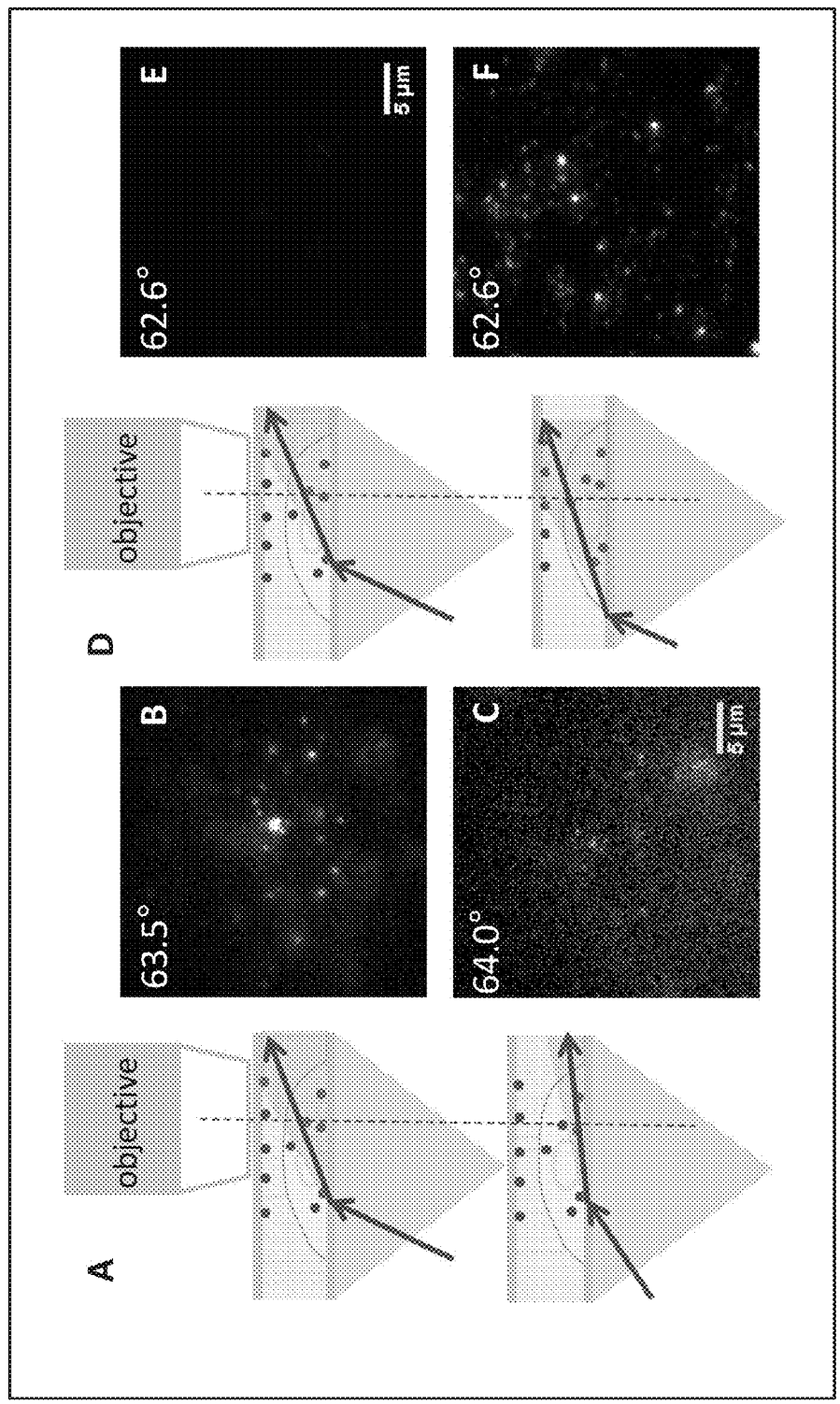
FIG. 11 are micrographs of illustrations of control of illumination field depth according to embodiment two.

FIG. 11. Illumination field depth controlled by changing the incident angle or the horizontal laser spot at the interface of cell culture and glass substrate. (A) Schematic diagram showing the illumination field at two incident angles. (B, C) The fluorescence images at two incident angles of 63.5° and 64.0°. The objective's focal plane was fixed at 2 μm away from the cell basolateral membrane. A group of fluorescent nanospheres were imaged at 63.5°, but disappeared at 64.0° due to the shallower illumination field depth at a larger incident angle. (D) Schematic diagram showing the illumination field at the same incident angle but different horizontal positions of the laser spot. (E, F) The fluorescence images at the same incident angle of 62.6° but two different horizontal positions of the laser spot. The objective's focal plane was fixed at the top coverslip. The fluorescent nanospheres absorbed to the top coverslip were not imaged when the laser spot was close to the objective's field of view. They were imaged when the laser spot was moved further away from the objective's field of view.

C. Options and Alternatives

As can be appreciated by those skilled in the art, system 10 and its methodology can be applied to other samples and other applications in analogous ways. Exemplary embodiment one provides examples of observation of live cells, observation of single molecules, and other samples. Variations obvious to those skilled in the art are included within the invention. The invention is not limited to the exemplary embodiment.

It can be seen how the invention achieves at least all of its stated objects, features, aspects, and advantages. But it can be applied in analogous ways to other applications with variations obvious to those skilled in the art. There are many biological or chemical applications for the system and method. System 10 can find incident angles in the full relevant range for VA-TIRM (from subcritical angles to nearly 90°) with an interval as small as on the order of 0.02°. As can be appreciated by those skilled in the art, these angles can vary according to set up and other parameters. Also, the new auto-calibration is fast relative to present manual re-calibration methods (a matter of a few minutes). Super axial resolution, improved over the state of the art, is possible.

One example of a option of the invention is that the dual color laser sub-system could be created as original equipment to system 10. Alternatively, it could be an add-on module that could be retro-fitted to basic TIRM hardware. The new software could be installed on the computer for system 10 to operate the add-on module.

By further example, the basic concepts of the exemplary embodiment can be implemented in different configurations. For example, they could be implemented in a TIRFM or TIRM microscope that is inverted from the position shown in FIG. 1A.

Another example would be operation with a single laser. The new auto-calibration and auto-scanning can be beneficially applied to just one laser. But also, more than two lasers are possible by utilizing a third laser and associated mirrors, shutter, focusing lens, and controllable adjustable mirror relative to prism 18. The system is thus expandable, so to speak, according to need or desire.

1. Alternative Microscope Configuration

Figure 1E:
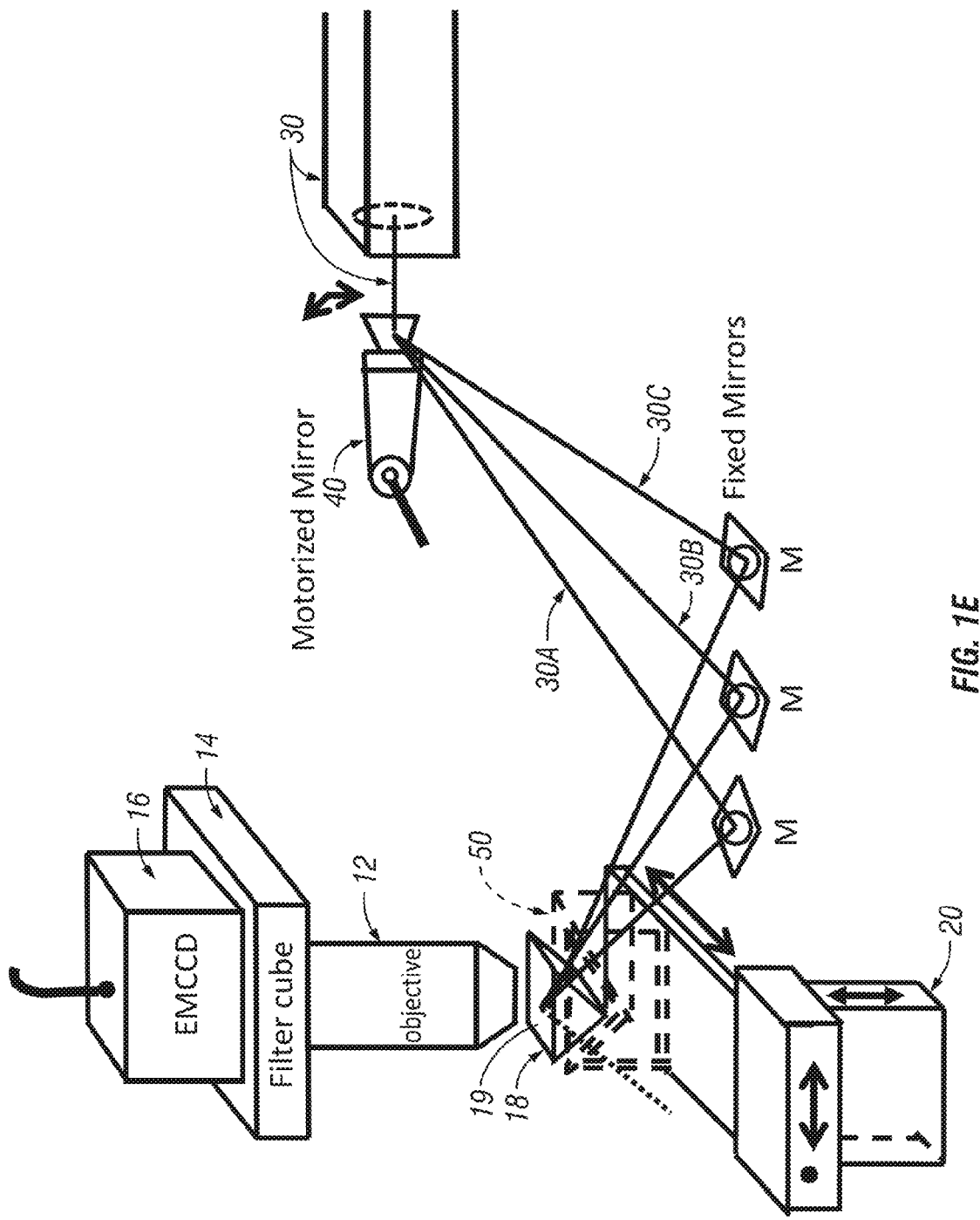
FIG. 1E is a schematic diagram of an alternative embodiment of a VA-TIRFM imaging microscope according to the invention.

FIG. 1E illustrates schematically an alternative configuration for the microscope. Instead of two lasers 30 and 31 as in FIG. 1A, a single laser 30 can be projected to mirror galvanometer 40, which can be configured to split beam 30 into plural beams 30A-C. Each beam portion 30A-C could be directed to a fixed mirror M. Control of single mirror galvanometer 40 can alter angle of incidence of each beam portion 30A-C at the slide/sample interface of a slide at the base 19 of prism 18.

There can be benefits to using the system of FIG. 1A over that of FIG. 1E, and visa versa. For example, the system of FIG. 1E might simplify the design and/or avoid the use of some motorized linear stages. Fast scanning can be accomplished with reset of only the voltage of the motorized mirror (mirror galvanometer 40). This can be on the order of and perhaps more accurate and precise than the system of FIG. 1A. On the other hand, this system of FIG. 1E may limit the number of available incident angles to accommodate fixed mirrors M and the angle range of motorized mirror 40.

On the other hand, the system of FIG. 1A can efficiently be used for any incident angle in a range from the critical angle to 90 degrees. Calibration is fast and accurate. It is easy to set up a scan with more than 100 steps. However, the scanning/imaging may not be as fast. Reproducibility and precision of vertical motorized stages may place some limits on vertical resolution.

But either configuration of FIGS. 1A and 1E present advantages over the state of the art.

2. Optional Heating Method for Sample

Figure 1F:
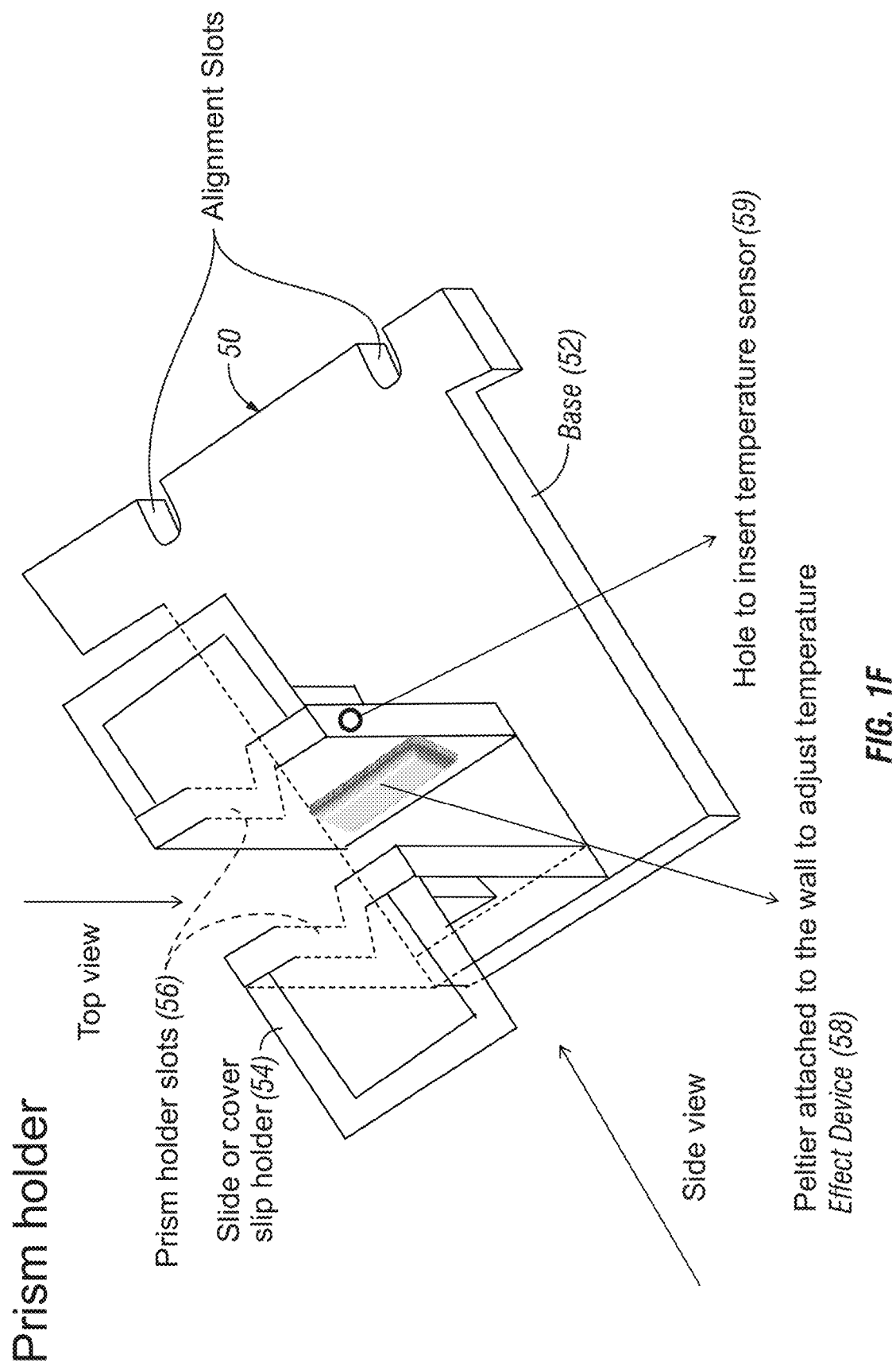
FIG. 1F is an enlarged perspective view of a prism and sample holder that can be used with the microscopes of either FIG. 1A or 1E.
Figure 1G:
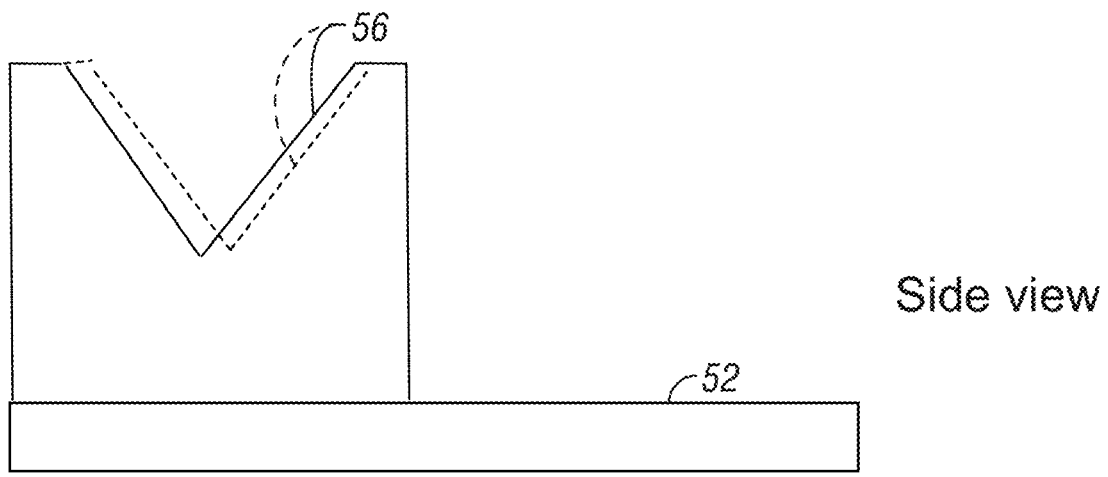
FIGS. 1G and 1H are side and top isometric views of the prism and sample holder of FIG. 1F.
Figure 1H:
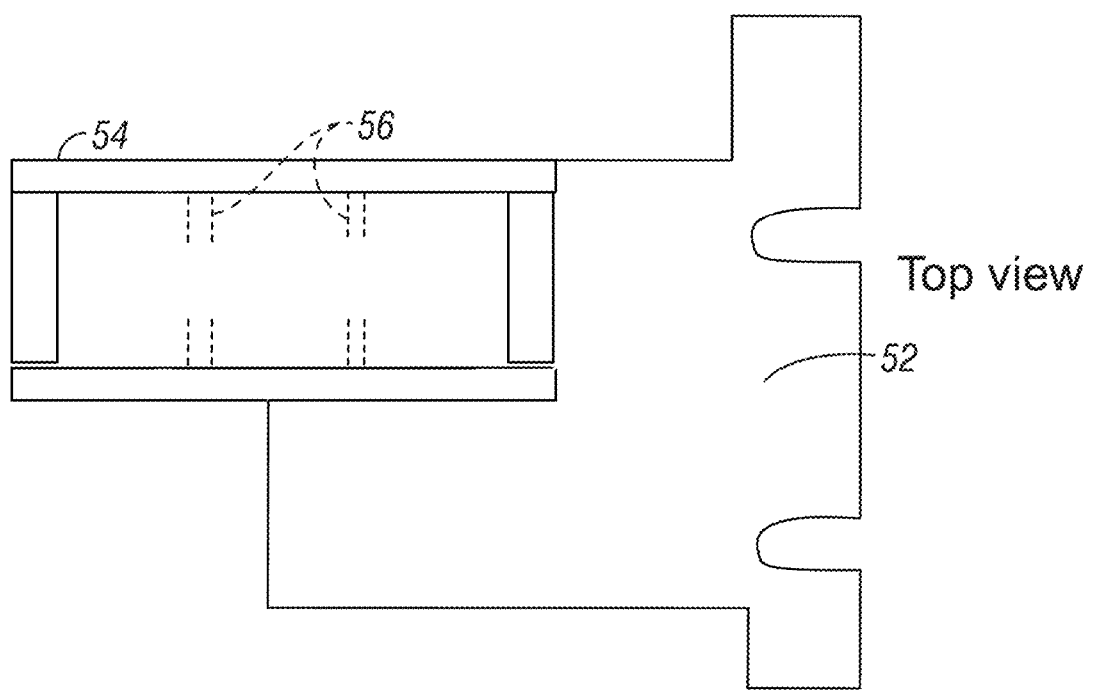

FIG. 1F illustrates an option for the prism/slide holder 50. It can be desirable, in certain circumstance, to maintain a certain temperature at or around the sample position. A thermoelectric cooling component 58 could be mounted adjacent the slide or cover slip holder 54 portion of the prism/slide holder 50 and be selectively operated to maintain a certain temperature at or around that area. One example for component 58 is a Peltier effect device, such as are well-known and commercially available. Thermoelectric cooling uses the Peltier effect to create a heat flux between the junction of two different types of materials. A Peltier cooler, heater, or thermoelectric heat pump is a solid-state active heat pump which transfers heat from one side of the device to the other side against the temperature gradient (from cold to hot), with consumption of electrical energy. Such an instrument is also called a Peltier device, Peltier diode, cooling diode, Peltier heat pump, solid state refrigerator, or thermoelectric cooler. Because heating can be achieved more easily and economically by many other methods, Peltier devices are mostly used for cooling. However, when a single device is to be used for both heating and cooling, a Peltier device may be desirable. Simply connecting it to a DC voltage will cause one side to cool, while the other side warms. The effectiveness of the pump at moving the heat away from the cold side is dependent upon the amount of current provided and how well the heat can be removed from the hot side. As indicated in FIG. 1F, a temperature sensor (not shown) could be mounted in a temperature sensor aperture 59 in the holder 50 to monitor temperature. Feedback from temperature sensor could be used to control operation of the thermal electric device 58 according to need or desire.

3. Other Forms of TIRM

As mentioned, the concepts of the TIRFM methods of apparatus described herein can be also applied to other TIRM microscopy that does not necessarily require fluorescence-based detection. A few alternative detection modes are Raman effect scattering, plasmonic scattering, and surface plasmon resonance. Others are possible. The techniques of exemplary embodiments one and two can be applied to other TIRM modes.

REFERENCES

Yim, Sang-Youp et al., "Total Internal Reflection Microscopy for Surface Plasmon Scattering of a Single Cu Nanowire" Lasers and Electro-Optics—Pacific Rim, 2007. CLEO/Pacific Rim 2007.

McKee, Kristopher J. et al., "Variable Angle Total Internal Reflection Raman Microscopy", Conference Oct. 10, 2008.

Smith, David R., "Plasmon Resonant Nanoparticles" The Research Group of David R. Smith, Novel Electromagnetic Materials, Duke University.

Smith, David R.m "Dark-Field Microscopy, Jan. 31, 2007, Duke Center for Surface Plasmonids: Plasmon Nanoparticles.

McKee, Kristopher J. et al., "Development of a scanning angle total internal reflection Raman spectrometer", AIP Review of Scientific Instruments, Vol. 81, Issue 4, 043106 (2010), 6 pages.

Yang, Shu-Chun et al., "Plasmon Hybridization in Individual Gold Nanocrystal Dimmers: Direct Observation of Bright and Dark Modes", NANO Lett., DOI:10.1021/n1903693v.

What is claimed:

1. A method of prism-type TIR microscopy comprising:
    (a) providing a prism-type TIR microscope with an objective lens having an optical axis and an excitation laser adjustable over a range of angles of incidence between sub-critical TIR angles to nearly 90 degrees to create an illumination spot at or near a prism or slide/sample interface in the microscope's field of view and at or near the optical axis of the objective lens by controlled actuation of one or more laser beam adjustment components between reproducible settings;

(b) pre-calibrating the microscope at plural incident angles over the range of angles of incidence of the excitation laser by:
  (i) placing immobilized fluorescing nanoparticles at the prism or slide/sample interface;
  (ii) automatically actuating at least one of the one or more laser beam adjustment components to direct the laser through the prism and create the illumination spot at or near the optical axis of the objective lens, and at a first of the plural incident angles in the range;
  (iii) automatically actuating at least one of the one or more laser beam adjustment components to move the illumination spot to plural locations around and including the first location while measuring fluorescence intensity from at least some of the fluorescing nanoparticles;
  (iv) comparing measured fluorescence intensity at each of the locations;
  (v) automatically selecting one of the locations as indicative of overlap of the illumination spot with the optical axis of the objective lens for the first of the plural incident angles based on the comparison of measured fluorescence intensities;
  (vi) storing the reproducible settings related to the one or more adjustment components corresponding to the selected location of the illumination spot for the first of the plurality of the incident angles;
  (vii) repeating steps (i)-(vi) for each of the other angles of incidence to provide calibrated reproducible settings for overlap of the illumination spot with the optical axis of the objective lens for each of the plurality of incident angle;

(c) providing a sample at the prism or slide/sample interface;

(d) automatically adjusting angle of incidence of the excitation laser by retrieving and actuating the one or more laser beam adjustment components to the stored calibrated reproducible settings for each of the plural incident angles so that the illumination spot is automatically optimized relative to the microscope's field of view at each of the incident angles; and (e) imaging the sample at each of the plural incident angles.

2. The method of claim 1 wherein the automatic optimization comprises automatically overlapping the laser beam illumination spot in the sample with the center of the microscope's field of view.

3. The method of claim 1 wherein the precisely controlled intervals comprise intervals smaller than 0.2°.

4. The method of claim 1 further comprising automatically adjusting angle of incidence of a second laser beam relative to the slide/sample interface according to step (d) of claim 1, wherein the second laser beam differs in color than the said laser beam.

5. The method of claim 1 wherein steps (a) and (b) comprise an automatic calibration of the microscope for each sample by incremental coarse angle of incidence adjustment, a fine angle of incidence adjustment, or both, while monitoring changes to total fluorescence signal in a specified area for each angle.

6. The method of claim 5 wherein the automatic calibration coarse angle increments are approximately ten times larger than fine angle increments and calibration for all angles is accomplished in no more than several minutes.

7. The method of claim 1 further comprising using step (d) to precisely and automatically scan the sample.

8. The method of claim 7 further comprising imaging the sample on each scan and storing the images.

9. The method of claim 8 further comprising using the stored images to reconstruct the sample in 3D.

10. The method of claim 1 used in VA-TIRFM.

11. The method of claim 1 used in pseudo-TIRFM.

12. The method of claim 1 applied to observation and imaging of:
  (a) one or more live cells; or
  (b) single molecules.

13. The method of claim 1 wherein the TIR microscope comprises a VA-TIRFM microscope system.

14. The method of claim 1 wherein the TIR microscope comprises a VA TIR Raman scattering microscope system.

15. The method of claim 1 wherein the TIR microscope comprises a plasmonic scattering microscope system.

16. The method of claim 1 wherein the microscopy comprises SPR imaging.

17. The method of claim 1 where the TIR microscope gathers scattered light.

18. An apparatus for prism-type TIR microscopy comprising:
  (a) a prism-type TIR microscope including an objective lens having an optical axis adapted to present a sample at a prism/sample interface with a microscope slide in the microscope's field of view;
  (b) an first actuator to adjust position of the sample/slide interface to the microscope field of view;
  (c) an second actuator to adjust angle of incidence of a laser beam relative to the prism of the prism-type TIR microscope;
  (d) a programmable controller operatively connected to the first and second actuators;
  (e) a program installed on the programmable controller, the program adapted to:
    i. automatically control at least one of the first actuator and the second actuator to adjust angle of incidence of a laser beam relative the prism of the prism-type TIR microscope and relative to the prism/sample interface a range of angles from subcritical TIR angles to nearly 90° by precisely controlled intervals to create a laser beam illumination spot relative the microscope's field of view at a first location at Or near the prism or slide/sample interface, at or near the optical axis of the objective lens, and at a first of the plural incident angles in the range;
  (f) using step (e) for pre-calibrating the microscope over the range of angles of incidence by:
    (i) placing immobilized fluorescing nanoparticles at the prism/sample interface;
    (ii) automatically adjusting at least one of the first and second actuators between reproducible settings to direct the laser through the prism at a first incident angle in the range to move the illumination spot to plural locations around and including the first location;
    (iii) measuring fluorescence intensity from at least some of the fluorescing nanoparticles;
    (iv) comparing measured fluorescence intensity at each of the locations;
    (v) automatically selecting one of the locations as indicative of overlap the illumination spot with the optical axis of the objective lens for the first of the incident angles based on the comparison of measured fluorescence intensities;

(vi) storing the reproducible settings related to the adjustment of the first and/or second actuators corresponding to the selected location of the illumination spot for the first of the plurality of incident angles;

(vii) repeating steps (f)(i)-(vi) for each of the other angles of incidence to provide calibrated reproducible settings for overlap of the illumination spot with the optical axis of the objective lens for each of the plurality of incident angles;

(g) using step (e) to scan a sample.

19. The apparatus of claim 18 further comprising automatically overlapping the laser beam illumination spot on the sample with the center of the microscope's field of view.

20. The apparatus of claim 18 wherein the precisely controlled intervals comprises intervals smaller than 0.2°.

21. The apparatus of claim 18 further comprising automatically adjusting angle of incidence of a second laser beam relative to the slide/sample interface according to step (g) of claim 18, wherein the second laser beam differs in color than the said laser beam.

22. The apparatus of claim 18 wherein steps (e) and (f) comprise an automatic calibration of the microscope for each sample.

23. The apparatus of claim 18 further comprising a frame adapted to hold the prism of the prism-type TIR microscope in a fixed position relative to a slide or coverslip receiver on the microscope stage and including a heating and/or cooling component at or near the sample position.

24. The apparatus of claim 18 further comprising using step (g) to precisely and automatically scan the sample.

25. The apparatus of claim 24 further comprising imaging the sample on each scan and storing the images.

26. The apparatus of claim 25 further comprising using the stored images to reconstruct the sample in 3D.

27. The apparatus of claim 18 applied to observation and imaging of:
(a) one or more live cells; or
(b) single molecules.

28. The apparatus of claim 18 wherein the TIR microscope comprises a plasmonic scattering microscope system.

29. The apparatus of claim 18 adapted for SPR imaging.

30. The apparatus of claim 18 where the TIR microscope gathers scattered light.

31. A prism-type TIR microscope comprising:
(a) a microscope objective lens having a optical axis;
(b) an imaging camera along the optical axis;
(c) a slide on the base of the prism, the slide including a sample location;
(d) a stage actuator operatively connected to the stage to move the stage in multiple-degrees of freedom of movement relative to the objective lens;
(e) a first laser beam source capable of generating a first laser beam of a pre-determined color along a first laser beam path;
(f) an adjustable mirror in the first laser beam path;
(g) a first actuator operatively connected to the adjustable mirror in the first laser beam path to change the direction of the first laser beam relative to a side of the prism;
(h) a second laser beam source capable of generating a second laser beam of a pre-determined color different than the first laser beam along a second laser beam path;
(i) an adjustable mirror in the second laser beam path;
(j) a second actuator operatively connected to the adjustable mirror in the second laser beam path to change the direction of the second laser beam relative to a side of the prism;

(k) so that the first and second laser beams and prism can be adjusted by precisely controllable actuators to provide two color illumination of a sample over a range of TIR angles and the stage actuator can assist in automatic optimization of either laser beam relative to the sample location and the optical axis of the microscope objective lens, the automatic optimization comprising automatically actuating at least one of the first and second actuators and associated adjustable mirror, having reproducible positions, to direct its laser beam through the prism and create an illumination spot from the laser at a first location at or near the prism/sample interface at or near the optical axis of the objective lens and at a first of the plural incident angles in the range, automatically actuating the at least one of the first and second actuators and associated adjustable mirror to move the illumination spot to plural locations around and including the first location while measuring fluorescence intensity, comparing measured fluorescence intensity at each of the locations, automatically selecting one of the locations as indicative of overlap of the illumination with the optical axis of the objective lens based on the comparison of measured fluorescence intensities, and storing the reproducible settings of the at least one of the first and second actuators and associated adjustable mirror corresponding to the selected location.

32. The microscope of claim 31 further comprising a filter between the camera and the objective lens along the optical axis.

33. The microscope of claim 31 wherein the imaging camera is capable of video.

34. The microscope of claim 31 further comprising one or more additional laser beam sources and associated mirror and actuator.

35. The microscope of claim 31 further comprising a controller with software to control the actuators.

36. The microscope of claim 35 wherein the software controls automatic calibration of the laser beams relative to the sample over a range of critical TIR angles for each sample.

37. The microscope of claim 36 wherein the range of critical TIR angles comprise less than 0.2° increments.

38. The microscope of claim 31 wherein the VA-TIR microscopy comprises a VA-TIRFM microscope system.

39. The microscope of claim 31 wherein the VA-TIR microscope comprises a VA TIR Raman scattering microscope system.

40. The microscope of claim 31 wherein the VA-TIR microscope comprises a plasmonic scattering microscope system.

41. The microscope of claim 31 adapted for SPR imaging.

42. A method of VA-TIR microscopy comprising:
a. initializing controllable, adjustable VA-TIR hardware;
b. inputting ranges and intervals for incident angles;
c. calibrating for a range of incident angles by:
   i. resetting the hardware to maximum or minimum positions relative to the range;
   ii. calibrating the hardware for each of a plurality of incremental angles along the range based on changes to total fluorescence signal and storing those calibrations for each incremental angle the automatic optimization comprising automatically actuating at least one laser beam adjustment component having reproducible positions to direct the laser through the prism and create an illumination spot from the laser at a first location at or near the prism/sample interface at or near the optical axis of the objective lens, and at a first of the plural incident angles in the range, automatically actuating the at least one laser beam adjustment component to move the illumination spot to plural location around and including the first location while measuring fluorescence intensity, comparing measured fluorescence intensity at each of the locations, automatically selecting one of the locations as indicative of overlap of the illumination spot within the optical axis of the objective lens based on the comparison of measured fluorescence intensities, and storing the reproducible settings of the at least one adjustment component corresponding to the selected location;
  d. resetting the system;
  e. selecting a scanning method;
  f. scanning through at least some of the calibrated incremental angles;
  g. collecting images at each scanned angle; and
  h. resolving vertical positions from the images.

43. The method of claim 42 wherein the calibrating comprises one or both of:
  a. coarse calibration where incremental angles are larger;
  b. fine calibration where incremental angles are smaller.

44. The method of claim 43 wherein incremental angles of coarse calibration are approximately ten times larger than incremental angles for fine calibration.

45. A method of microscopy comprising:
  a. automatically calibrating a TIR microscope having an objective lens with an optical axis and an adjustable angle-of-incidence excitation laser beam illumination spot relative to sample location at or near the optical axis of the objective lens by optimizing the illumination spot relative to the objective lens axis for each of a plurality of angles-of-incidence over a range of angles-of-incidence; the optimizing comprising pre-calibrating the microscope over the range of angles of incidence by:
    (i) placing immobilized fluorescing nanoparticles at a prism or slide/sample interface;
    (ii) automatically adjusting at least one laser beam adjustment component having reproducible settings to direct the laser through the prism at a first incident angle in the range and create the illumination spot at a first location at or near the prism or slide/sample interface, at or near the optical axis of the objective lens, and at a first or the plural incident angles in the range;
    (iii) automatically actuating the at least one laser beam adjustment component to move the illumination spot to plural locations around and including the first location while measuring fluorescence intensity;
    (iv) comparing measured fluorescence intensity at each of the locations;
    (v) automatically selecting one of the locations as indicative of overlap of the illumination spot with the optical axis of the objective lens for the first of the plural incident angles based on the comparison of measured fluorescence intensities;
    (vi) storing the reproducible settings related to the at least one adjustment component corresponding to selected location of the illumination spot for the first of the plurality of incident angles;
    (vii) repeating steps (a)(i)-(vi) for each of the other angles of incidence to provide calibrated reproducible settings for overlap of the illumination spot with the optical axis of the objective lens for each of the plurality of incident angles;
  b. controlling the excitation laser beam over the range to collect images or a signal relating to a sample at one or more of a plurality of calibrated angles-of-incidence.

46. The method of claim 45 wherein illumination field depth is controlled by changing incident angle of the laser beam or position of the excitation laser illumination spot relative the sample.

47. The method of claim 45 further comprising combining both scanning at incident angles in sub-critical range and incident angles larger than critical angle.

48. The method of claim 47 wherein the TIR microscope comprises a plasmonic scattering microscope system.

49. The method of claim 45 adapted for SPR imaging.

50. The method of claim 45 where the TIR microscope gathers scattered light.

* * * * *

UNITED STATES PATENT AND TRADEMARK OFFICE
CERTIFICATE OF CORRECTION

| | |
|---|---|
| PATENT NO. | : 9,012,872 B1 |
| APPLICATION NO. | : 13/006739 |
| DATED | : April 21, 2015 |
| INVENTOR(S) | : Ning Fang et al. |

It is certified that error appears in the above-identified patent and that said Letters Patent is hereby corrected as shown below:

In the claims

Col. 25, Claim 1(b)(vii), Line 36:
DELETE after incident "angle"
ADD after incident --angles--

Col. 26, Claim 18(e), line 41:
ADD after interface --over--

Col. 26, Claim 18 (e)(i), line 45:
DELETE after location at "Or"
ADD after location at --or--

Col. 26, Claim 18(f)(v), lines 64-65:
ADD after overlap --of--
ADD after of the --plural--

Col. 28, Claim 31(k), line 13:
ADD --,-- after lens

Col. 28, Claim 31(k), line 21:
ADD after illumination --spot--

Col. 29, Claim 42(c)(ii), line 3:
DELETE "location"
ADD --locations--

Signed and Sealed this
Sixth Day of October, 2015

Michelle K. Lee
*Director of the United States Patent and Trademark Office*

CERTIFICATE OF CORRECTION (continued)
U.S. Pat. No. 9,012,872 B1

Col. 29, Claim 42 (c)(ii), line 7:
DELETE after spot "within"
ADD after spot --with--

Col. 30, Claim 48, line 35:
DELETE after claim "47"
ADD after claim --45--